US010810213B2

(12) United States Patent
Jung et al.

(10) Patent No.: US 10,810,213 B2
(45) Date of Patent: Oct. 20, 2020

(54) PHENOTYPE/DISEASE SPECIFIC GENE RANKING USING CURATED, GENE LIBRARY AND NETWORK BASED DATA STRUCTURES

(71) Applicant: Illumina, Inc., San Diego, CA (US)

(72) Inventors: Marc Jung, Sunnyvale, CA (US); Sam Ng, Menlo Park, CA (US); Joseph R. Delaney, Hayward, CA (US)

(73) Assignee: Illumina, Inc., San Diego, CA (US)

( * ) Notice: Subject to any disclaimer, the term of this patent is extended or adjusted under 35 U.S.C. 154(b) by 249 days.

(21) Appl. No.: 15/723,055

(22) Filed: Oct. 2, 2017

(65) Prior Publication Data
US 2018/0095969 A1    Apr. 5, 2018

Related U.S. Application Data

(60) Provisional application No. 62/403,206, filed on Oct. 3, 2016.

(51) Int. Cl.
| | |
|---|---|
| *G06F 16/2457* | (2019.01) |
| *G16B 5/00* | (2019.01) |
| *G16B 30/00* | (2019.01) |
| *G16B 20/00* | (2019.01) |
| *G06F 17/15* | (2006.01) |
| *G06F 17/16* | (2006.01) |

(52) U.S. Cl.
CPC ........ *G06F 16/24578* (2019.01); *G06F 17/15* (2013.01); *G06F 17/16* (2013.01); *G16B 5/00* (2019.02); *G16B 20/00* (2019.02); *G16B 30/00* (2019.02)

(58) Field of Classification Search
CPC ....................................................... G06F 17/15
See application file for complete search history.

(56) References Cited

U.S. PATENT DOCUMENTS

| | | | |
|---|---|---|---|
| 2007/0162411 A1 | 7/2007 | Kupershmidt et al. | |
| 2009/0049019 A1 | 2/2009 | Su et al. | |
| 2018/0080082 A1* | 3/2018 | Mougeot | C12Q 1/6883 |

FOREIGN PATENT DOCUMENTS

CN        102855398 A      1/2013

OTHER PUBLICATIONS

Komurov et al., "An integrated network platform for contextual prioritization of drugs and pathways", 2015 (Year: 2015).*

(Continued)

*Primary Examiner* — Dawaune A Conyers
(74) *Attorney, Agent, or Firm* — Weaver Austin Villeneuve & Sampson LLP

(57) ABSTRACT

The present invention relates to methods, systems and apparatus for capturing, integrating, organizing, navigating and querying large-scale data from high-throughput biological and chemical assay platforms. It provides a highly efficient meta-analysis infrastructure for performing research queries across a large number of studies and experiments from different biological and chemical assays, data types and organisms, as well as systems to build and add to such an infrastructure. According to various embodiments, methods, systems and interfaces for identifying genes that are potentially associated with a biological, chemical or medical concept of interest.

29 Claims, 22 Drawing Sheets

(56) References Cited

OTHER PUBLICATIONS

Ghiassian, S. et al., "ADiseAse MOdule Detection (DIAMOnD) Algroithm Derived from a Systematic Analysis of Connectivity Patterns of Disease Proteins in the Human Interactome", PLoS Comput Biol 11(4) E1004120 Doi:10.1371/journal.pcbi.1004120, 2015.

Mukherjee, S. et al., "Gene Ranking Using Bootstrapped P-values", Sigkdd Explorations vol. 5 (2), 2003, 14-20.

Simoes, S. et al., "NERI: network-medicine based integrative approach for disease gene prioritization by relative importance", BMC Bioinformatics 16(Suppl 9): S9, 2015.

Bacon, C. et al., "Brain-specific Foxp1 deletion impairs neuronal development and causes autistic-like behaviour", Molecular Psychiatry 20 2015, 623-639.

Nava, C. et al., "Hypomorphic variants of cationic amino acid transporter 3 in males with autism spectrum disorders", Amino Acids 47, 2015, 2647-2658.

Shen, K. et al., "Meta-analysis for pathway enrichment analysis when combining mutiple genomic studies", Gene expression vol. 26 No. 10, 2010, 1316-1326.

Shi, L. et al., "Whole-genome sequencing in an autism multiplex family", Molecular Autism 4:8, 2013.

Xiao, Y. et al., "Differential expression pattern-based priortization of candidate genes through integrating disease-specific expression data", Genomics 98, 2011, 64-71.

\* cited by examiner

|  | Test | Validation |  |
|---|---|---|---|
| Gene Rank | Gene Values | Gene Values | Penalty |
| 1 | 98 | 93 | 1 |
| 2 | 95 | 87 | 1 |
| 3 | 93 | 92 | 1 |
| 4 | 92 | 95 | 1 |
| 5 | 90 | 78 | 1 |
| 6 | 88 | 65 | 0.95 |
| 7 | 85 | 83 | 0.95 |
| 8 | 83 | 75 | 0.95 |
| 9 | 82 | 80 | 0.95 |
| 10 | 80 | 65 | 0.95 |
| 11 | 78 | 64 | 0.9 |
| 12 | 77 | 63 | 0.9 |
| 13 | 75 | 59 | 0.9 |
| 14 | 74 | 67 | 0.9 |
| 15 | 72 | 58 | 0.9 |
| 16 | 60 | 60 | 0.85 |
| 17 | 65 | 43 | 0.85 |
| 18 | 63 | 53 | 0.85 |
| 19 | 61 | 60 | 0.85 |
| 20 | 57 | 47 | 0.85 |

Rows 1-5: Bucket #1
Rows 6-10: Bucket #2
Rows 11-15: Bucket #3
Rows 16-20: Bucket #4

FIG. 9

| P1 | Experimental | | | In silico | | | Knowledge-based | | Rank |
| --- | --- | --- | --- | --- | --- | --- | --- | --- | --- |
| | S1 | S2 | S3 | S1* | S2* | S3* | PPI | GO | |
| Gene1 | 92 | | | $f_P(43)$ | | $f_P(23)$ | | | 3 |
| Gene2 | | 87 | | | $f_P(54)$ | | $f_{PPI}(21)$ | $f_{GO}(54)$ | 4 |
| Gene3 | 63 | 32 | | | | | | | 2 |
| Gene4 | | 100 | | $f_P(99)$ | | $f_P(43)$ | | | 1 |
| Gene5 | | | 10 | $f_P(21)$ | $f_P(44)$ | | | | 7 |
| Gene6 | 32 | | 32 | $f_P(34)$ | | | $f_{PPI}(23)$ | $f_{GO}(43)$ | 5 |
| Gene7 | | | 32 | $f_P(88)$ | $f_P(54)$ | | | | 6 |
| Gene8 | | 11 | | | | $f_P(43)$ | | | 10 |
| Gene9 | | | 31 | | | | | | 8 |
| Gene10 | | | | $f_P(88)$ | $f_P(88)$ | $f_P(90)$ | $f_{PPI}(80)$ | $f_{GO}(90)$ | 9 |
| Gene11 | | | | | | $f_P(21)$ | | | 11 |
| Gene12 | | | | $f_P(99)$ | $f_P(32)$ | | | $f_{GO}(32)$ | 12 |
| Gene13 | | | | | | | $f_{PPI}(80)$ | | 13 |

| P1 | S1 |
|---|---|
| Gene1 | 92 |
| Gene2 |  |
| Gene3 | 63 |
| Gene4 |  |
| Gene5 |  |
| Gene6 | 32 |
| Gene7 |  |
| Gene8 |  |
| Gene9 |  |
| Gene10 |  |
| Gene11 |  |
| Gene12 |  |
| Gene13 |  |

1204

| Gene1 | S04 | S05 | S06 | S07 | RMS |
|---|---|---|---|---|---|
| Gene2 | 78 |  |  |  | 42.7 |
| Gene3 |  | 56 |  |  | 28.0 |
| Gene4 | 18 |  | 78 |  | 40.0 |
| Gene5 |  |  | 47 | 56 | 36.6 |
| Gene6 |  |  |  |  |  |
| Gene7 |  |  |  |  |  |
| Gene8 |  |  |  |  |  |
| Gene9 |  |  |  |  |  |
| Gene10 |  |  |  |  |  |
| Gene11 |  |  |  |  |  |
| Gene12 |  |  |  |  |  |
| Gene13 |  |  |  |  |  |

1206

| Gene3 | S08 | S09 | S10 | RMS |
|---|---|---|---|---|
| Gene1 | 38 |  |  | 44.0 |
| Gene2 | 66 | 18 |  | 10.4 |
| Gene3 |  |  |  |  |
| Gene4 |  | 35 |  | 22.7 |
| Gene5 |  | 47 |  | 27.1 |
| Gene6 | 39 | 18 |  | 24.8 |

1208

| Gene6 | S11 | S12 | S13 | S14 | S15 | RMS |
|---|---|---|---|---|---|---|
| Gene1 |  | 54 | 43 | 38 |  | 35.2 |
| Gene2 |  | 78 |  | 35 |  | 38.2 |
| Gene3 |  | 39 |  | 88 |  | 43.0 |
| Gene4 |  | 66 |  | 78 |  | 45.7 |
| Gene5 | 56 |  |  |  |  | 57.3 |
| Gene6 |  |  |  |  |  |  |
| Gene7 | 47 |  | 64 |  | 47 | 41.3 |
| Gene8 | 38 | 34 |  | 39 |  | 23.1 |
| Gene9 | 89 |  | 32 |  | 45 | 26.3 |
| Gene10 |  |  | 65 | 66 | 89 | 65.1 |
| Gene11 |  | 47 |  |  |  | 29.1 |
| Gene12 |  |  |  |  |  | 21.0 |
| Gene13 | 42 |  | 22 |  | 32 | 25.6 |

1210

| G1,3,6 | Gene1 RMS | Gene3 RMS | Gene6 RMS | S1* |
|---|---|---|---|---|
| Gene1 |  | 44.0 | 35.2 | 32.5 |
| Gene2 | 42.7 | 10.4 | 38.2 | 33.7 |
| Gene3 | 28.0 |  | 43.0 | 29.6 |
| Gene4 | 40.0 | 22.7 | 45.7 | 37.4 |
| Gene5 | 36.6 | 27.1 | 57.3 | 42.3 |
| Gene6 | 21.5 | 24.8 |  | 18.9 |
| Gene7 | 30.2 | 21.9 | 41.3 | 32.1 |
| Gene8 | 58.7 | 42.2 | 23.1 | 43.8 |
| Gene9 | 19.0 | 10.4 | 26.3 | 19.7 |
| Gene10 | 55.4 | 54.8 | 65.1 | 58.6 |
| Gene11 | 38.5 | 56.1 | 29.1 | 42.7 |
| Gene12 | 27.0 | 31.2 | 21.0 | 26.7 |
| Gene13 | 21.0 | 20.8 | 25.6 | 22.6 |

FIG. 12

| P1 | Experimental | | | In silico | | | Knowledge base | | Rank |
|---|---|---|---|---|---|---|---|---|---|
| | S1 | S2 | S3 | S1* | S2* | S3* | PPI | GO | |
| Gene1 | 92 | | | $f_p(43)$ | | $f_p(23)$ | | | 3 |
| Gene2 | | 87 | | | $f_p(54)$ | | $f_{PPI}(21)$ | $f_{GO}(54)$ | 4 |
| Gene3 | 63 | 32 | | | | | | | 2 |
| Gene4 | | 100 | 10 | $f_p(99)$ | | $f_p(43)$ | | | 1 |
| Gene5 | | | | $f_p(21)$ | $f_p(44)$ | | | | 7 |
| Gene6 | 32 | | 32 | $f_p(34)$ | | | $f_{PPI}(23)$ | | 5 |
| Gene7 | | 11 | 32 | $f_p(88)$ | $f_p(54)$ | | | $f_{GO}(43)$ | 6 |
| Gene8 | | | 31 | | | $f_p(43)$ | | | 10 |
| Gene9 | | | | | | | | | 8 |
| Gene10 | | | | $f_p(88)$ | $f_p(88)$ | $f_p(90)$ | $f_{PPI}(80)$ | $f_{GO}(90)$ | 9 |
| Gene11 | | | | $f_p(99)$ | | $f_p(21)$ | | | 11 |
| Gene12 | | | | | $f_p(32)$ | | | $f_{GO}(32)$ | 12 |
| Gene13 | | | | | | | $f_{PPI}(80)$ | | 13 |

FIG. 15

$S'G_i \sim SG_i + \sum ((SG_i + SG_n)*EdgeWeight)$
Wherein $S'G_i$ is an interactome score for gene $G_i$,
$SG_i$ is a summary score for gene $G_i$,
$SG_n$ is a summary score for gene $G_n$ that is directly connected to $G_i$, and
EdgeWeight is a weight assigned to the edge connecting $G_i$ and $G_n$ based on knowledge base data

PHENOTYPE/DISEASE SPECIFIC GENE RANKING USING CURATED, GENE LIBRARY AND NETWORK BASED DATA STRUCTURES

CROSS REFERENCE TO RELATED APPLICATIONS

This application claims benefits under 35 U.S.C. § 119(e) to U.S. Provisional Patent Application No. 62/403,206, entitled: PHENOTYPE/DISEASE SPECIFIC GENE RANKING USING CURATED, GENE LIBRARY AND NETWORK BASED DATA STRUCTURES, filed Oct. 3, 2016, which is herein incorporated by reference in its entirety for all purposes.

BACKGROUND

The present disclosure relates generally to methods, systems and apparatus for storing and retrieving biological, chemical and medical information. Research in these fields has increasingly shifted from the laboratory bench to computer-based methods. Public sources such as NCBI (National Center for Biotechnology Information), for example, provide databases with genetic and molecular data. Between these and private sources, an enormous amount of data is available to the researcher from various assay platforms, organisms, data types, etc. As the amount of biomedical information disseminated grows, researchers need fast and efficient tools to quickly assimilate new information and integrate it with pre-existing information across different platforms, organisms, etc. Researchers also need tools to quickly navigate through and analyze diverse types of information.

There are growing pharmaceutical and clinical needs to screen for potential biomarkers in order to advance personalized treatment options or to identify new diseases for existing drugs to be effective. Identifying disease specific genes in cancer and complex diseases is challenging and time-consuming. A complex disease is usually characterized by a few related disease phenotypes which are affected by complex genetic factors through different biological pathways. These pathways are likely to overlap and interact with one another leading to more intricate network. The conventional pathway-base gene ranking can provide limited value in various situations. Identification of genes that are associated with these phenotypes will help understand the mechanism of the disease development in a comprehensive manner.

In this context, a problem to be solved is to identify the closest genes associated with a given phenotype or other biological, chemical and medical concepts. For example, given a phenotype, such as prostate cancer, can a gene panel of arbitrary size be identified? Using conventional approaches, given the disease, months of review and analysis of various sources such as journals, online database, experimental data, in person discussions and exchanges may lead to a gene set. This process can take months or longer.

Various implementations of the disclosure provides technology to identify the most significant genes given phenotype or other biological, chemical, or pharmaceutical concepts of interest. Based on large database including curated gene regulation data (e.g., RNA expression, protein expression, DNA methylation, transcription factor activity, and association level in genome wide association study) as well as comprehensive correlation between gene regulation data on the one hand and gene set data and interactome data on the other hand.

SUMMARY

The present invention relates to methods, systems and apparatus for capturing, integrating, organizing, navigating and querying large-scale data from high-throughput biological and chemical assay platforms. It provides a highly efficient meta-analysis infrastructure for performing research queries across a large number of studies and experiments from different biological and chemical assays, data types and organisms, as well as systems to build and add to such an infrastructure. Embodiments of the invention provide methods, systems and interfaces for associating experimental data, features and groups of data related by structure and/or function with chemical, medical and/or biological terms in an ontology or taxonomy. Embodiments of the invention also provide methods, systems and interfaces for filtering data by data source information, allowing dynamic navigation through large amounts of data to find the most relevant results for a particular query.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the operations including: (a) selecting, by the one or more processors, a plurality of gene sets from a database, wherein each gene set of the plurality of gene sets includes a plurality of genes and a plurality of experimental values associated with the plurality of genes, and wherein the plurality of experimental values are correlated with the biological, chemical or medical concept of interest in at least one experiment; (b) determining, for each gene set and by the one or more processors, one or more experimental gene scores for first one or more genes among the plurality of genes using one or more experimental values of the first one or more genes; (c) determining, for each gene set and by the one or more processors, one or more in silico gene scores for second one or more genes among the plurality of gene sets based at least in part on the first one or more genes' correlations with the second one or more genes, wherein the first one or more genes' correlations with the second one or more genes are indicated in other gene sets in the database beside the plurality of gene sets; (d) obtaining, by the one or more processors, summary scores for the first and second one or more genes based at least in part on the one or more experimental gene scores for the first one or more genes determined in (b) and the one or more in silico gene scores for the second one or more genes determined in (c), wherein each summary score is aggregated across the plurality of gene sets; and (e) identifying, by the one or more processors, the genes that are potentially associated with the biological, chemical or medical concept of interest using the summary scores of the first and second one or more genes.

Implementations may include one or more of the following features. In some implementations, (c) includes, for each gene set of the plurality of gene sets: (i) identifying a second plurality of gene sets from the database, each gene set of the second plurality of gene sets including a second plurality of genes and a second plurality of experimental values associated with the second plurality of genes, and where the second plurality of experimental values are correlated with a first gene among the first one or more genes. The method may also include (ii) aggregating the experimental values across the second plurality of gene sets to obtain a vector of aggregated values for the first gene among the first one or more genes. The method may also include (iii) applying (i) and (ii) to one or more other genes among the first one or more genes, thereby obtaining one or more vectors of experimental values for the one or more other genes among the first one or more genes. The method may also include (iv) aggregating vectors of aggregated values for the first gene and the one or more other genes among the first one or more genes, thereby obtaining one compressed vector including the one or more in silico gene scores for the second one or more genes.

Also provides is a method where each of the aggregated vectors of (iv) for a particular gene among the first one or more genes is weighted in proportion to an experimental value of the particular gene. The method where each of the aggregated vectors of (iv) for a particular gene among the first one or more genes is weighted in proportion to a number of gene sets of the second plurality of gene sets identified for the particular gene.

Some implementations provide the method further including, determining, before (d), one or more gene-group scores for third one or more genes. Some implementations provide the method where each gene-group score for a particular gene is determined using (i) gene memberships of one or more gene groups that each include a group of genes related to a group label, where the group of genes includes the particular gene, and (ii) at least some of the one or more experimental values of the first one or more genes.

Some implementations provide the method where (d) includes obtaining the summary scores for the first and second one or more genes based at least in part on the gene-group scores for at least some of the third one or more genes, as well as the one or more experimental scores for the first one or more genes determined in (b) and the one or more in silico scores for the second one or more genes determined in (c).

Some implementations provide the method where determining the one or more gene-group scores for the third one or more genes includes: identifying, for a particular gene among the third one or more genes, the one or more gene groups that each include the particular gene. The method may also include determining, for each gene group, a percentage of members of the gene group that are among the first one or more genes. The method may also include aggregating, for each gene group, one or more experimental values of at least some of the first one or more genes that are members of the gene group, thereby obtaining a sum experimental value for the gene group. The method may also include determining, for the particular gene among the third one or more genes, a gene-group score using the percentage of members of the gene group that are among the first one or more genes and the sum experimental value for the gene group.

Some implementations provide the method where determining the gene-group score using the percentage of members of the gene group that are among the first one or more genes and the sum experimental value for the gene group includes: obtaining, for each gene group, a product of the percentage of members and the sum experimental value, thereby obtaining one or more products for the one or more gene groups. The method may also include summing, across the one or more gene groups, the one or more products, thereby obtaining a summed product. The method may also include determining, for the particular gene among the third one or more genes, a gene-group score based on the summed product.

Some implementations provide the method where the plurality of genes related to the group label include genes in a gene set library.

In some implementations, the genes in a gene set library include genes in a gene ontology. In some implementations, the group label indicates a condition, an attribute, a disease, a phenotype, a syndrome, a trait, a biological function, a biological pathway, a cell, an organism, a biological function, a compound, a treatments, etc.

In some implementations, the method further includes, before (d), determining interactome scores respectively for fourth one or more genes. In some implementations, each interactome score for a particular gene is determined using (i) connections between the particular gene and other genes connected to the particular gene in a network of genes and (ii) at least some of the one or more experimental values of the first one or more genes. In some implementations, (d) includes obtaining the summary scores for at least the first one or more genes and the second one or more genes based at least in part on the interactome scores for at least some of the fourth one or more genes, as well as the one or more experimental gene scores for the first one or more genes determined in (b) and the one or more in silico gene scores for the second one or more genes determined in (c). In some implementations, the network of genes are based on inter-actions and relations among genes, proteins, and/or phospholipids.

In some implementations, determining interactome scores respectively for the fourth one or more genes includes: providing a network of genes, wherein each pair of genes in the network are connected by an edge, the genes of the network include the fourth one or more genes, which include at least some of the first one or more genes and/or the second one or more genes; defining, for each gene of the fourth one or more genes, a neighborhood of connected genes based on a connection distance from a particular gene as measured by the number of connection edges connecting two adjacent genes; and calculating, for each gene of the fourth one or more genes, an interactome score using (i) one or more connection distances between the particular gene and one or more other genes in the neighborhood and (ii) summary scores of the one or more other genes in the neighborhood, wherein the summary scores are based on experimental data.

In some implementations, the interactome score is calculated as proportional to a sum of multiple fractions, each fraction being a summary score of another gene in the neighborhood divided by a connection distance between the particular gene and the other gene in the neighborhood.

In some implementations, determining interactome scores respectively for fourth one or more genes includes: providing a network of genes, wherein the genes of the network have summary scores based on experimental data above a first threshold value, each pair of genes are connected by an edge, and the genes of the network include the fourth one or more genes, which include at least some of the first one or more genes and/or the second one or more genes; assigning, for each edge, a weight to the edge connecting two genes based on connection data for the two genes in at least one intereactome knowledge base; and calculating, for each gene in the network, an interactome score using (i) weights of edges between a particular gene and all genes connected to the particular gene, and (ii) summary scores of all genes connected to the particular gene.

In some implementations, calculating the interactome score includes calculating the interactome score as $N_i'$:

$$N_i' = N_i + \Sigma((N_i + N_n) * \text{edge\_weight}_n)$$

wherein $N_i$ is the summary score of the particular gene i, $N_n$ is a summary score of gene n connected to the particular gene, and $\text{edge\_weight}_n$ is the weight of the edge connecting the particular gene i and gene n.

In some implementations, calculating the interactome score further includes: saving $N_i'$ that are smaller than a second threshold in a first pass dictionary; and repeating the calculation for all genes in the first pass dictionary, thereby updating the interactome scores. In some implementations, calculating the interactome score further includes repeating the calculation for one or more passes.

In some implementations, selecting the plurality of experimental gene sets of (a) includes selecting experimental gene sets based on biotag scores assigned to biotags associated with the experimental gene sets, wherein the biotag scores indicate levels of importance of gene sets. In some implementations, the biotags are organized by categories selected from the group consisting of biosource, biodesign, tissue, disease, compound, gene, genemode, biogroup, and any combination thereof. In some implementations, the method further includes performing scoring of gene sets and/or gene groups based on biotags.

In some implementations, the plurality of experimental values include variant or gene associated data wherein a specific relation from a data value to a gene or multiple genes can be derived. In some implementations, the plurality of experimental values includes a plurality of gene perturbation values. In some implementations, wherein the plurality of experimental values indicate levels of RNA expression, protein expression, DNA methylation, transcription factor activity, and/or association in genome wide association study.

In some implementations, the biological, chemical or medical concept of interest includes a phenotype. In some implementations, the phenotype includes a disease-related phenotype.

In some implementations, each summary score of a particular gene is calculated as a linear combination of the experimental scores and in silico scores across the plurality of gene sets.

In some implementations, (d) includes: providing a model that receives as inputs experimental gene scores and in silico gene scores and provides as outputs summary scores; and applying the model to the one or more experimental gene scores and the one or more in silico gene scores to obtain the summary scores for the first one or more genes and the second one or more genes.

In some implementations, the method further includes training the model by optimizing an objective function. In some implementations, training the model includes applying a bootstrap technique to bootstrap samples. In some implementations, the objective function relates to at least one summary score distribution after bootstrapping. In some implementations, optimizing the objective function includes minimizing differences of summary scores between a training set and a validation set. In some implementations, optimizing the objective function includes maximizing a distance between a summary score distribution obtained from the plurality of gene sets and a summary score distribution obtained from random gene sets.

In some implementations, summary scores are ranked and binned in buckets of a defined size, wherein penalty scores are assigned to the buckets, the penalty scores favoring higher ranked summary scores. In some implementations, the objective function is based only on top ranked summary scores.

In some implementations, training the model includes using the objective function in an unsupervised machine learning approach to learn parameters of the model.

In some implementations, the model has the form $$F(\theta) = k1*c1 + k2*c2 + \ldots + kn*cn$$

wherein $\theta$ are parameters of the model, ci are components of the model, and ki are weight factors for the components.

In some implementations, the method further includes partitioning one or more of the components of the model into sub-components based on sample weights of experimental data types.

In some implementations, the summary scores of the first and second one or more genes are penalized based on how likely experimental values of the first and second one or more genes in one or more random gene sets are correlated with the biological, chemical or medical concept of interest. In some implementations, each summary score of a particular gene is penalized by a penalty value that is inversely proportional to a p value of a rank product, wherein the rank product includes a product of ranks of the particular gene across the one or more random gene sets.

In some implementations, the first one or more genes are not identical to the second one or more genes.

In some implementations, the summary scores are normalized.

In some implementations, the database includes a plurality of sub-databases.

In some implementations, one or more experimental values of the first one or more genes in (b) meet a criterion.

In some implementations, each summary score is aggregated by means of linear combination of singular values. In some implementations, the linear combination involves a sum of squares.

One general aspect includes a computer program product including a non-transitory machine readable medium storing program code that, when executed by one or more processors of a computer system, causes the computer system to implement a method for identifying genes that are potentially associated with a biological, chemical or medical concept of interest, said program code including: (a) code for selecting a plurality of gene sets from a database, where each gene set of the plurality of gene sets includes a plurality of genes and a plurality of experimental values associated with the plurality of genes, and where the plurality of experimental values are correlated with the biological, chemical or medical concept of interest in at least one experiment. The program code also includes (b) code for determining, for each gene set, one or more experimental gene scores for first one or more genes among the plurality of genes using one or more experimental values of the first one or more genes. The program code also includes (c) code for determining, for each gene set, one or more in silico gene scores for second one or more genes among the plurality of genes based at least in part on the first one or more genes' correlations with the second one or more genes, where the first one or more genes' correlations with the second one or more genes are indicated in other gene sets in the database beside the plurality of gene sets. The program code also includes (d) code for obtaining summary scores for the first and second one or more genes based at least in part on the one or more experimental gene scores for the first one or more genes determined in (b) and the one or more in silico gene scores for the second one or more genes determined in (c), where each summary score is aggregated across the plurality of gene sets. The program code also includes (e) code for identifying the genes that are potentially associated with the biological, chemical or medical concept of interest using the summary scores of the first and second one or more genes.

Another general aspect includes a computer system, including: one or more processors. The computer system also includes system memory; and one or more computer-readable storage media having stored thereon computer-executable instructions that, when executed by the one or more processors, cause the computer system to implement a method for identifying genes that are potentially associated with a biological, chemical or medical concept of interest, the method including: (a) selecting, by the one or more processors, a plurality of gene sets from a database, where each gene set of the plurality of gene sets includes a plurality of genes and a plurality of experimental values associated with the plurality of genes, and where the plurality of experimental values are correlated with the biological, chemical or medical concept of interest in at least one experiment; (b) determining, for each gene set and by the one or more processors, one or more experimental gene scores for first one or more genes among the plurality of genes using one or more experimental values of the first one or more genes; (c) determining, for each gene set and by the one or more processors, one or more in silico gene scores for second one or more genes among the plurality of genes based at least in part on the first one or more genes' correlations with the second one or more genes, where the first one or more genes' correlations with the second one or more genes are indicated in other gene sets in the database beside the plurality of gene sets; (d) obtaining, by the one or more processors, summary scores for the first and second one or more genes based at least in part on the one or more experimental gene scores for the first one or more genes determined in (b) and the one or more in silico gene scores for the second one or more genes determined in (c), where each summary score is aggregated across the plurality of gene sets; and (e) identifying, by the one or more processors, the genes that are potentially associated with the biological, chemical or medical concept of interest using the summary scores of the first and second one or more genes.

Embodiments of the invention provide methods for associating experimental data, features and groups of data related by structure and/or function with chemical, medical and/or biological terms in an ontology or taxonomy. In certain embodiments, the data analyzed by the methods described are typically noisy and imperfect. The methods filter out noisy genes to make the predictions. Also provided are methods of querying various types of data in a database (including features, feature sets, feature groups, and tags or concepts) to produce a list of the most relevant or significant genes in the database in response to the query.

Computer program products and computer systems for implementing any of the above methods are provided. These and other aspects of the invention are described further below with reference to the drawings.

BRIEF DESCRIPTION OF THE DRAWINGS

FIG. 9 shows data for illustrating optimizing the objective function.

FIG. 10 shows schematic data for obtaining gene ranks according to some implementations.

FIG. 12 shows illustrative data for a gene set S1 correlated with phenotype P1.

FIG. 15 illustrates the experimental values for members Ii of the gene group that are among the experimental gene sets G1 to G3.

DETAILED DESCRIPTION

Introduction and Relevant Terminology

Figure 1:
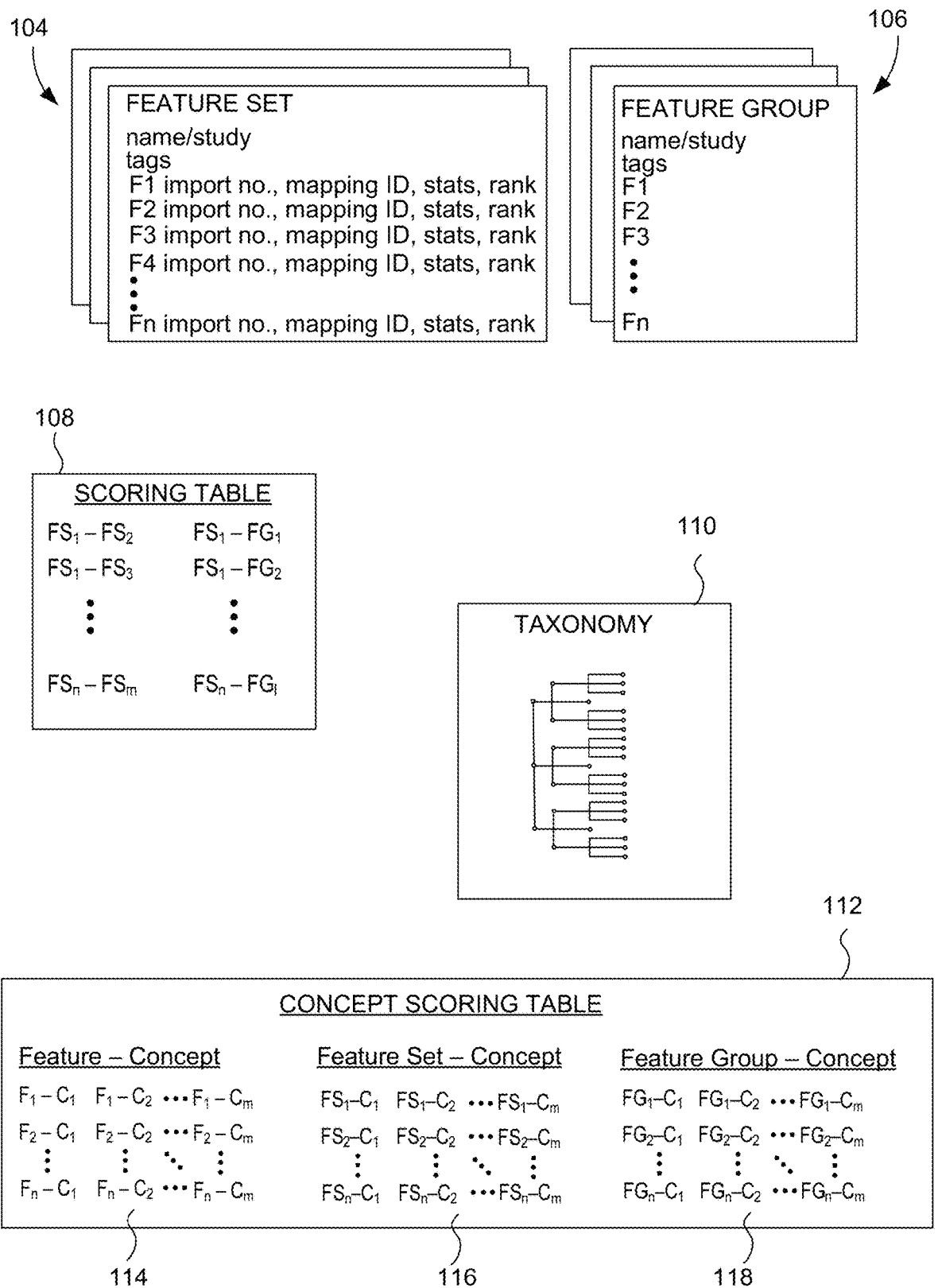
FIG. 1 is a representation of various elements in the Knowledge Base of scientific information according to various embodiments of the invention.

Implementations of the disclosure have various applications, such as in precision medicine by matching patient data with phenotype derived gene ranking, and in drug screening by optimizing gene ranking lists for drug combinations.

In some implementations, the disclosure provides gene ranking technologies for disease, phenotype, and other biological, chemical, or medical concepts that utilize the power of DNA expression data to make accurate and sound predictions of candidate genes with high value and relevance to the specific concepts. Some implementations can identify connections to diseases or treatments of interest, which connections will evolve as correlation experimental correlation data content gross. Some implementations can provide disease specific RNA, DNA, or epigenetic panels on the fly, which can increase the chance of discovering new biomarkers. New and improved analysis may be performed when new data is integrated into the correlation database. Some implementations can leverage the power of drug perturbation data derived from databases to find drug or compound combinations that correlate with a disease of interest.

In some implementations, the method and systems utilize big data in a curated database for RNA-based expression studies, wherein the data are embedded in a hierarchical framework. The underlying database can organically grow over time expanding breadth and depth of coverage. Some implementations involves bio-tagging, based on, e.g., bio-designs and biosources, which ensures that the analysis is focused on the most valuable and relevant data. Various implementations provide methods and systems for identifying disease specific genes not present in other RNA expression analysis tools.

In some implementations, the problem of phenotype specific gene ranking or concept specific gene ranking is solved by using curated datatypes including RNA expression, trait associated gene mutations, DNA methylation and other gene related data structure, which are referred to as polyomics or multiomics data herein. Moreover, knowledge base information such as ontology based information, as well as network-based information such as protein-protein interactions are used to identify the relevant genes. In some implementations, a unsupervised machine learning framework is implemented to obtain summary scores from the multiple sources of information above. In some implementations, a bootstrapping approach is used to generate more robust ranking structures. In some implementations, top score evaluation instead of whole gene rank evaluation is applied, which can filter out randomly enriched perturbation signals. In some implementations, this is achieved by using probabilistic rank product scores on shuffled gene sets. In addition, in some implementations, a biotag prioritization technique is used identify the optimal gene sets for each curated study related to a given phenotype or concept in the curated database.

In some implementations, experimental data based summary scores are used in combination with graph models or network models. In some implementations, connection edges in a gene network are defined by external knowledge base such as protein-protein interactions (PPI) or gene set libraries.

In some implementations, parameters of a model incorporating the approaches above are optimized by an unsupervised machine learning technique, e.g., by minimizing summary scores differences between test data and validation data, and/or by maximizing the difference between concept-specific gene scores and randomly generated gene scores.

Conventional approaches use non-curated data structures and/or seed genes derived from data sources such as Online Mendelian Inheritance in Man (OMIM). Also, conventional methods using non-curated data do not allow for gene prioritization based on biotags.

Interactome data refers to data that relate the state of two genes. The relation of two genes may be based on statistical correlations between the two genes and other data sources and studies. The interactions or relations between the two genes may be related to their functions, structures, biological pathways, transcription factor, promoter, and other factors. In various implementations, interactome data provides a basis to form a network of contacted nodes and connections between the nodes, wherein the nodes present genes. Conventional gene networks sometimes include highly connected nodes, which may result from artifacts. In other words, genes may be connected with each other in the network that the connections do not underlie the biological or chemical concept of interest, such as a disease. In many conventional network based gene studies, seed genes are required to develop a network. The networks include limited experimental data. Also, information and data underlying the network are often rigid and inflexible.

Various implementations of the disclosure provides methods for identifying genes that are highly correlated with the concept of interest, which concepts may be disease, phenotype, the syndrome, a trait, a biological function, a biological pathway, compound, a treatment, medical condition, and other biological, chemical, and medical concepts. The methods use experimental data of genes that are correlated with or regulated by the concept of interest. The methods also use in silico data that are based on correlations among genes and gene sets. In some implementations, the methods also use knowledge based data in addition to the experimental gene data and the in silico gene data.

The present invention relates to methods, systems and apparatus for capturing, integrating, organizing, navigating and querying large-scale data from high-throughput biological and chemical assay platforms. It provides a highly efficient meta-analysis infrastructure for performing research queries across a large number of studies and experiments from different biological and chemical assays, data types and organisms, as well as systems to build and add to such an infrastructure.

While most of the description below is presented in terms of systems, methods and apparatuses that integrate and allow exploration of data from biological experiments and studies, the invention is by no means so limited. For example, the invention covers chemical and clinical data. In the following description, numerous specific details are set forth in order to provide a thorough understanding of the present invention. It will be apparent, however, that the present invention may be practiced without limitation to some of the specific details presented herein.

The following terms are used throughout the specification. The descriptions are provided to assist in understanding the specification, but do not necessarily limit the scope of the invention.

The term concept is used herein to refer to biological, chemical, and medical concepts that can be correlated with genes or gene related data. Concepts refer to diseases, phenotypes, syndromes, traits, biological function, a biological pathway, cells, organism, biological functions, compounds, treatments, medical conditions, and other biological, chemical, and medical concepts.

Tag—A tag associates descriptive information about a feature set with the feature set. This allows for the feature set to be identified as a result when a query specifies or implicates a particular tag. Often clinical parameters are used as tags. Examples of tag categories include tumor stage, patient age, sample phenotypic characteristics and tissue types. In certain embodiments, tags may also be referred to as concepts because concepts may be used as tags.

Biotag are tags are associated with biological characteristics. Various categories and examples of biotags are further provided herein after.

Database—A database is an organized collection of data. In some implementations, a database includes data relating to a specific subject area, such as gene set theory or gene interactome. Such databases are also referred to as knowledge base. For instance, database may refer to a collection of data used to analyze and respond to queries. In certain embodiments, it includes one or more feature sets, feature groups, and metadata for organizing the feature sets in a particular hierarchy or directory (e.g., a hierarchy of studies and projects). In addition, a knowledge base may include information correlating feature sets to one another and to feature groups, a list of globally unique terms or identifiers for genes or other features, such as lists of features measured on different platforms (e.g., Affymetrix human HG_U133A chip), total number of features in different organisms, their corresponding transcripts, protein products and their relationships. A knowledge base typically also contains a taxonomy that contains a list of all tags (keywords) for different tissues, disease states, compound types, phenotypes, cells, as well as their relationships. For example, taxonomy defines relationships between cancer and liver cancer, and also contains keywords associated with each of these groups (e.g., a keyword "neoplasm" has the same meaning as "cancer"). Due to the specific contents of the database, it is also referred to as a knowledge base.

Correlation is any of a broad class of statistical relationships involving dependence between two variables or concepts. It is not required a linear relation or a causal relationship. It refers to is any statistical relationship, whether causal or not, between two random variables or two sets of data.

As an example, a new feature set input into the knowledge base is correlated with every other (or at least many) feature sets already in the knowledge base. The correlation compares the new feature set and the feature set under consideration on a feature-by-feature basis comparing the rank or other information about matching genes. A ranked based running algorithm is used in one embodiment (to correlate the feature sets). The result of correlating two feature sets is a "score." Scores are stored in the knowledge base and used in responding to queries about genes, clinical parameters, drug treatments, etc.

Correlation is also employed to correlate new feature sets against all feature groups in the knowledge base. For example, a feature group representing "growth" genes may be correlated to a feature set representing a drug response, which in turn allows correlation between the drug effect and growth genes to be made.

The term interactome is used to refer to the whole set of molecular interactions in a particular cell. The term specifically refers to physical interactions among molecules (such as those among proteins, also known as protein-protein interactions, PPIs) but can also describe sets of indirect interactions among genes.

Interactome data refers to data that relate the state of two genes. The relation of two genes may be based on statistical correlations between the two genes and other data sources and studies. The interactions or relations between the two genes may be related to their functions, structures, biological pathways, transcription factor, promoter, and other factors.

Raw data—This is the data from one or more experiments that provides information about one or more samples. Typically, raw data is not yet processed to a point suitable for use in the databases and systems of this invention. Subsequent manipulation reduces it to the form of one or more "feature sets" suitable for use in such databases and systems. The process of converting the raw data to feature sets is sometimes referred to as curation. Data are often tagged in the database, and the tagging are also referred to curation.

Most of the examples presented herein concern biological experiments in which a stimulus acts on a biological sample such as a tissue or cell culture. Often the biological experiment will have associated clinical parameters such as tumor stage, patient history, etc. The invention is not however limited to biological samples and may involve, for example, experiments on non-biological samples such as chemical compounds, various types of synthetic and natural materials, etc. and their effects on various types of assays (e.g., cancer cell line progression).

Whether working with biological or non-biological samples, the sample may be exposed to one or more stimuli or treatments to produce test data. Control data may also be produced. The stimulus is chosen as appropriate for the particular study undertaken. Examples of stimuli that may be employed are exposure to particular materials or compositions, radiation (including all manner of electromagnetic and particle radiation), forces (including mechanical (e.g., gravitational), electrical, magnetic, and nuclear), fields, thermal energy, and the like. General examples of materials that may be used as stimuli include organic and inorganic chemical compounds, biological materials such as nucleic acids, carbohydrates, proteins and peptides, lipids, various infectious agents, mixtures of the foregoing, and the like. Other general examples of stimuli include non-ambient temperature, non-ambient pressure, acoustic energy, electromagnetic radiation of all frequencies, the lack of a particular material (e.g., the lack of oxygen as in ischemia), temporal factors, etc. As suggested, a particularly important class of stimuli in the context of this invention is exposure to therapeutic agents (including agents suspected of being therapeutic but not yet proven to have this property). Often the therapeutic agent is a chemical compound such as a drug or drug candidate or a compound present in the environment. The biological impact of chemical compounds is manifest as a change in a feature such as a level of gene expression or a phenotypic characteristic.

As suggested, the raw data will include "features" for which relevant information is produced from the experiment. In many examples the features are genes or genetic information from a particular tissue or cell sample exposed to a particular stimulus.

A typical biological experiment determines expression or other information about a gene or other feature associated with a particular cell type or tissue type. Other types of genetic features for which experimental information may be collected in raw data include SNP patterns (e.g., haplotype blocks), portions of genes (e.g., exons/introns or regulatory motifs), regions of a genome of chromosome spanning more than one gene, etc. Other types of biological features include phenotypic features such as the morphology of cells and cellular organelles such as nuclei, Golgi, etc. Types of chemical features include compounds, metabolites, etc.

The raw data may be generated from any of various types of experiments using various types of platforms (e.g., any of a number of microarray systems including gene microarrays, SNP microarrays and protein microarrays, cell counting systems, High-Throughput Screening ("HTS") platforms, etc.). For example, an oligonucleotide microarray is also used in experiments to determine expression of multiple genes in a particular cell type of a particular organism. In another example, mass spectrometry is used to determine abundance of proteins in samples.

Feature set—This refers to a data set derived from the "raw data" taken from one or more experiments on one or more samples. The feature set includes one or more features (typically a plurality of features) and associated information about the impact of the experiment(s) on those features. At some point, the features of a feature set may be ranked (at least temporarily) based on their relative levels of response to the stimulus or treatment in the experiment(s) or based on their magnitude and direction of change between different phenotypes, as well as their ability to differentiate different phenotypic states (e.g., late tumor stage versus early tumor stage).

For reasons of storage and computational efficiency, for example, the feature set may include information about only a subset of the features or responses contained in the raw data. As indicated, a process such as curation converts raw data to feature sets.

Typically the feature set pertains to raw data associated with a particular question or issue (e.g., does a particular chemical compound interact with proteins in a particular pathway). Depending on the raw data and the study, the feature set may be limited to a single cell type of a single organism. From the perspective of a "Directory," a feature set belongs to a "Study." In other words, a single study may include one or more feature sets.

In many embodiments, the feature set is either a "bioset" or a "chemset." A bioset typically contains data providing information about the biological impact of a particular stimulus or treatment. The features of a bioset are typically units of genetic or phenotypic information as presented above. These are ranked based on their level of response to the stimulus (e.g., a degree of up or down regulation in expression), or based on their magnitude and direction of change between different phenotypes, as well as their ability to differentiate different phenotypic states (e.g., late tumor stage versus early tumor stage).

A feature set including genes and data related to the genes is a gene set. In this sense a gene set is also a type of bioset.

A chemset typically contains data about a panel of chemical compounds and how they interact with a sample, such as a biological sample. The features of a chemset are typically individual chemical compounds or concentrations of particular chemical compounds. The associated information about these features may be EC50 values, IC50 values, or the like.

A feature set typically includes, in addition to the identities of one or more features, statistical information about each feature and possibly common names or other information about each feature. A feature set may include still other pieces of information for each feature such as associated description of key features, user-based annotations, etc. The statistical information may include p-values of data for features (from the data curation stage), "fold change" data, and the like. A fold change indicates the number of times (fold) that expression is increased or decreased in the test or control experiment (e.g., a particular gene's expression increased "4-fold" in response to a treatment). A feature set may also contain features that represent a "normal state", rather than an indication of change. For example, a feature set may contain a set of genes that have "normal and uniform" expression levels across a majority of human tissues. In this case, the feature set would not necessarily indicate change, but rather a lack thereof.

In certain embodiments, a rank is ascribed to each feature, at least temporarily. This may be simply a measure of relative response within the group of features in the feature set. As an example, the rank may be a measure of the relative difference in expression (up or down regulation) between the features of a control and a test experiment. In certain embodiments, the rank is independent of the absolute value of the feature response. Thus, for example, one feature set may have a feature ranked number two that has a 1.5 fold increase in response, while a different feature set has the same feature ranked number ten that has a 5 fold increase in response to a different stimulus.

Directional feature set—A directional feature set is a feature set that contains information about the direction of change in a feature relative to a control. Bi-directional feature sets, for example, contain information about which features are up-regulated and which features are down-regulated in response to a control. One example of a bi-directional feature set is a gene expression profile that contains information about up and down regulated genes in a particular disease state relative to normal state, or in a treated sample relative to non-treated. As used herein, the terms "up-regulated" and "down-regulated" and similar terms are not limited to gene or protein expression, but include any differential impact or response of a feature. Examples include, but are not limited to, biological impact of chemical compounds or other stimulus as manifested as a change in a feature such as a level of gene expression or a phenotypic characteristic.

Non-directional feature sets contain features without indication of a direction of change of that feature. This includes gene expression, as well as different biological measurements in which some type of biological response is measured. For example, a non-directional feature set may contain genes that are changed in response to a stimulus, without an indication of the direction (up or down) of that change. The non-directional feature set may contain only up-regulated features, only down-regulated features, or both up and down-regulated features, but without indication of the direction of the change, so that all features are considered based on the magnitude of change only.

Feature group—This refers to a group of features (e.g., genes) related to one another. As an example, the members of a feature group may all belong to the same protein pathway in a particular cell or they may share a common function or a common structural feature. A feature group may also group compounds based on their mechanism of action or their structural/binding features.

Index set—The index set is a set in the knowledge base that contains feature identifiers and mapping identifiers and is used to map all features of the feature sets imported to feature sets and feature groups already in the knowledge base. For example, the index set may contain several million feature identifiers pointing to several hundred thousand mapping identifiers. Each mapping identifier (in some instances, also referred to as an address) represents a unique feature, e.g., a unique gene in the mouse genome. In certain embodiments, the index set may contain diverse types of feature identifiers (e.g., genes, genetic regions, etc.), each having a pointer to a unique identifier or address. The index set may be added to or changed as new knowledge is acquired.

Curation—Curation is the process of converting raw data to one or more feature sets (or feature groups). In some cases, it greatly reduces the amount of data contained in the raw data from an experiment. It removes the data for features that do not have significance. In certain embodiments, this means that features that do not increase or decrease significantly in expression between the control and test experiments are not included in the feature sets. The process of curation identifies such features and removes them from the raw data. The curation process also identifies relevant clinical questions in the raw data that are used to define feature sets. Curation also provides the feature set in an appropriate standardized format for use in the knowledge base.

Data import—Data import is the process of bringing feature sets and feature groups into a knowledge base or other repository in the system, and is an important operation in building a knowledge base. A user interface may facilitate data input by allowing the user to specify the experiment, its association with a particular study and/or project, and an experimental platform (e.g., an Affymetrix gene chip), and to identify key concepts with which to tag the data. In certain embodiments, data import also includes automated operations of tagging data, as well as mapping the imported data to data already in the system. Subsequent "preprocessing" (after the import) correlates the imported data (e.g., imported feature sets and/or feature groups) to other feature sets and feature groups.

Preprocessing—Preprocessing involves manipulating the feature sets to identify and store statistical relationships between pairs of feature sets in a knowledge base. Preprocessing may also involve identifying and storing statistical relationships between feature sets and feature groups in the knowledge base. In certain embodiments, preprocessing involves correlating a newly imported feature set against other feature sets and against feature groups in the knowledge base. Typically, the statistical relationships are pre-computed and stored for all pairs of different feature sets and all combinations of feature sets and feature groups, although the invention is not limited to this level of complete correlation.

In one embodiment, the statistical correlations are made by using rank-based enrichment statistics. For example, a rank-based iterative algorithm that employs an exact test is used in certain embodiments, although other types of relationships may be employed, such as the magnitude of overlap between feature sets. Other correlation methods known in the art may also be used.

As an example, a new feature set input into the knowledge base is correlated with every other (or at least many) feature sets already in the knowledge base. The correlation compares the new feature set and the feature set under consideration on a feature-by-feature basis by comparing the rank or other information about matching genes. A rank-based iterative algorithm is used in one embodiment to correlate the feature sets. The result of correlating two feature sets is a "score." Scores are stored in the knowledge base and used in responding to queries.

Study/Project/Library—This is a hierarchy of data containers (like a directory) that may be employed in certain embodiments. A study may include one or more feature sets obtained in a focused set of experiments (e.g., experiments related to a particular cardiovascular target). A Project includes one or more Studies (e.g., the entire cardiovascular effort within a company). The library is a collection of all projects in a knowledge base. The end user has flexibility in defining the boundaries between the various levels of the hierarchy.

Mapping—Mapping takes a feature (e.g., a gene) in a feature set and maps it to a globally unique mapping identifier in the knowledge base. For example, two sets of experimental data used to create two different feature sets may use different names for the same gene. Often herein the knowledge base includes an encompassing list of globally unique mapping identifiers in an index set. Mapping uses the knowledge base's globally unique mapping identifier for the feature to establish a connection between the different feature names or IDs. In certain embodiments, a feature may be mapped to a plurality of globally unique mapping identifiers. In an example, a gene may also be mapped to a globally unique mapping identifier for a particular genetic region. Mapping allows diverse types of information (i.e., different features, from different platforms, data types and organisms) to be associated with each other. There are many ways to map and some of these will be elaborated on below. One involves the search of synonyms of the globally unique names of the genes. Another involves a spatial overlap of the gene sequence. For example, the genomic or chromosomal coordinate of the feature in a feature set may overlap the coordinates of a mapped feature in an index set of the knowledge base. Another type of mapping involves indirect mapping of a gene in the feature set to the gene in the index set. For example, the gene in an experiment may overlap in coordinates with a regulatory sequence in the knowledge base. That regulatory sequence in turn regulates a particular gene. Therefore, by indirect mapping, the experimental sequence is indirectly mapped to that gene in the knowledge base. Yet another form of indirect mapping involves determining the proximity of a gene in the index set to an experimental gene under consideration in the feature set. For example, the experimental feature coordinates may be within 100 basepairs of a knowledge base gene and thereby be mapped to that gene.

Knowledge Base

FIG. 1 shows a representation of various elements in the Knowledge Base of scientific information according to various embodiments of the invention. Examples of generation of or addition to some of these elements (e.g., Feature Sets and a Feature Set scoring table) are discussed in U.S. patent application Ser. No. 11/641,539 (published as U.S. Patent Publication 20070162411), referenced above. The Knowledge Base may also include other elements such as an index set, which is used to map features during a data import process. In FIG. 1, element 104 indicates all the Feature Sets in the Knowledge Base. As is described in the U.S. Patent Publication 20070162411, after data importation, the Feature Sets typically contain at least a Feature Set name and a feature table. The feature table contains a list of features, each of which is usually identified by an imported ID and/or a feature identifier. Each feature has a normalized rank in the Feature Set, as well as a mapping identifier. Mapping identifiers and ranks may be determined during the import process, e.g., as described in U.S. Patent Publication 20070162411 and then may be used to generate correlation scores between Feature Sets and between Feature Sets and Feature Groups. The feature table also typically contains statistics associated with each feature, e.g., p-values and/or fold-changes. One or more of these statistics can be used to calculate the rank of each feature. In certain embodiments, the ranks may be normalized. The Feature Sets may also contain an associated study name and/or a list of tags. Feature Sets may be generated from data taken from public or internal sources.

Element 106 indicates all the Feature Groups in the Knowledge Base. Feature Groups contain a Feature Group name, and a list of features (e.g., genes) related to one another. A Feature Group typically represents a well-defined set of features generally from public resources—e.g., a canonical signaling pathway, a protein family, etc. Unlike Feature Sets, the Feature Groups do not typically have associated statistics or ranks. The Feature Sets may also contain an associated study name and/or a list of tags.

Element 108 indicates a scoring table, which contains a measure of correlation between each Feature Set and each of the other Feature Sets and between each Feature Set and each Feature Group. In the figure, FS1-FS2 is a measure of correlation between Feature Set 1 and Feature Set 2, FS1-FG1 a measure of correlation between Feature Set 1 and Feature Group 1, etc. In certain embodiments, the measures are p-values or rank scores derived from p-values.

Figure 2:
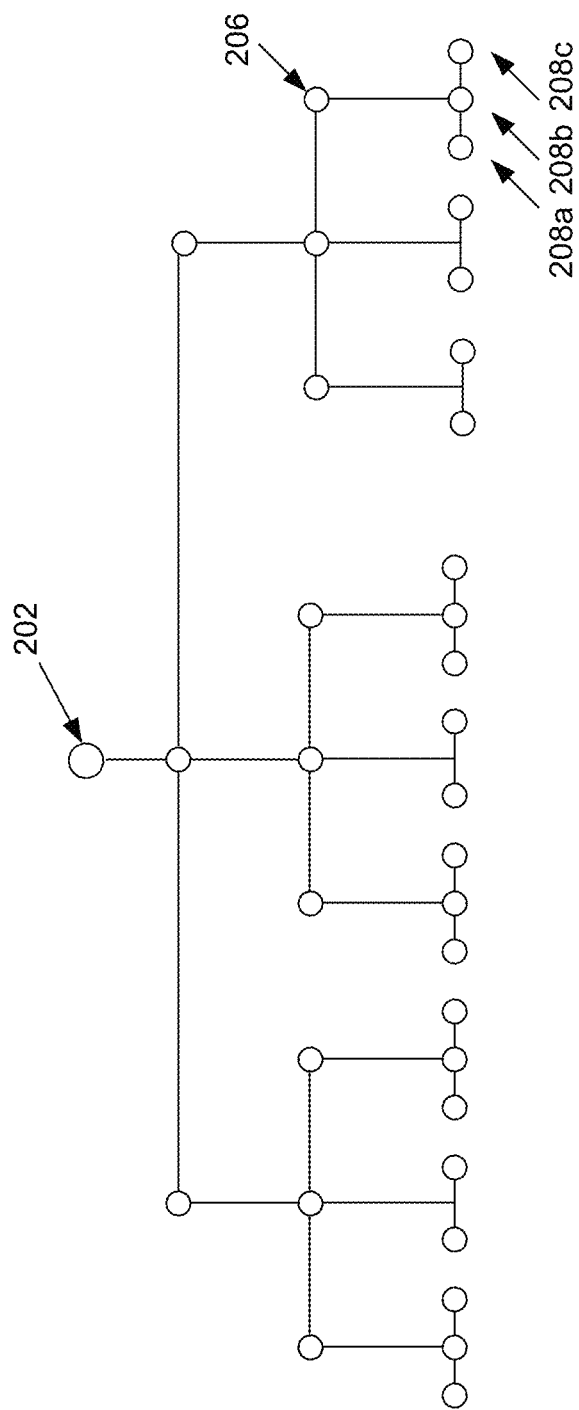
FIG. 2 is a representative schematic diagram of an ontology according to various embodiments of the invention.

Element 110 is a taxonomy or ontology that contains tags or scientific terms for different tissues, disease states, compound types, phenotypes, cells, and other standard biological, chemical or medical concepts as well as their relationships. The tags are typically organized into a hierarchical structure as schematically shown in the figure. An example of such a structure is Diseases/Classes of Diseases/Specific Diseases in each Class. The Knowledge Base may also contain a list of all Feature Sets and Feature Groups associated with each tag. The tags and the categories and sub-categories in the hierarchical structure are arranged in what may be referred to as concepts. A representative schematic diagram of an ontology is shown in FIG. 2. In FIG. 2, each node of the structure represents a medical, chemical or biological concept. Node 202 represents a top-level category, with children or sub-categories indicated by other nodes going down the tree, until the bottom-level concepts as indicated by node 208. In this manner, scientific concepts are categorized. For example, a categorization of stage 2 breast cancer may be: Diseases/Proliferative Diseases/Cancer/Breast Cancer/Stage 2 Breast Cancer, with disease the top-level category. Each of these—diseases, proliferative diseases, cancer, breast cancer and stage 2 breast cancer—is a medical concept that may be used to tag other information in the database. The taxonomy may be a publicly available taxonomy, such as the Medical Subject Headings (MeSH) taxonomy, Snomed, FMA (Foundation Model of Anatomy), PubChem Features, privately built taxonomies, or some combination of these. Examples of top-level categories include disease, tissues/organs, treatments, gene alterations, and Feature Groups.

Element 112 is a concept scoring table, which contains scores indicating the relevance of each concept or correlation of each concept with the other information in the database, such as features, Feature Sets and Feature Groups. In the embodiment depicted in FIG. 1, scores indicating the relevance of each concept in the taxonomy to each feature are shown at 114, scores indicating the relevance of each concept in the taxonomy to each Feature Set are shown at 116 and scores indicating the relevance of each concept in the taxonomy to each Feature Group are shown at 118. (As with the other elements represented in FIG. 1, the organizational structure of the concept scoring is an example; other structures may also be used to store or present the scoring.) In the figure, F1-C1 is a measure of relevance of Concept 1 to Feature 1, FS1-C1 a measure of relevance to Concept 1 to Feature Set 1; and FG1-C1 a measure of relevance to Concept 1 to Feature Group 1, etc. In certain embodiments, the concept scoring table includes information about the relevance or correlation of at least some concepts with each of all or a plurality of other concepts.

As discussed further below, the scores are stored for use in user queries to the Knowledge Base. Concept scoring allows a scientist querying the Knowledge Base to filter out the most relevant conditions for a query of interest. Users can quickly identify the top disease states, tissues, treatments and other entities associated with a query of interest. Also, as discussed below, concept scoring allows users to query concepts to find the most relevant features, Feature Sets and Feature Groups associated with the concept.

Generally, concept scoring involves i) identifying all Feature Sets having the concept under consideration, and ii) using the normalized rank of features within the identified Feature Sets or the pre-computed correlation scores of other Feature Sets or Feature Groups with the identified Feature Sets to determine a score indicating the relevance of the concept under consideration to each feature, Feature Set and Feature Group in the Knowledge Base. The concept scores can then be used to quickly identify the most relevant concepts for a particular feature, Feature Set or Feature Group. In certain embodiments, less relevant Feature Sets are removed prior to determining a score. For example, experiments done in a cell line may have little to do with the original disease tissue source for the cell line. Accordingly, in certain embodiments, Feature Sets relating to experiments done on this cell line may be excluded when computing scores for the disease concept.

Concept Scoring

Figure 3:
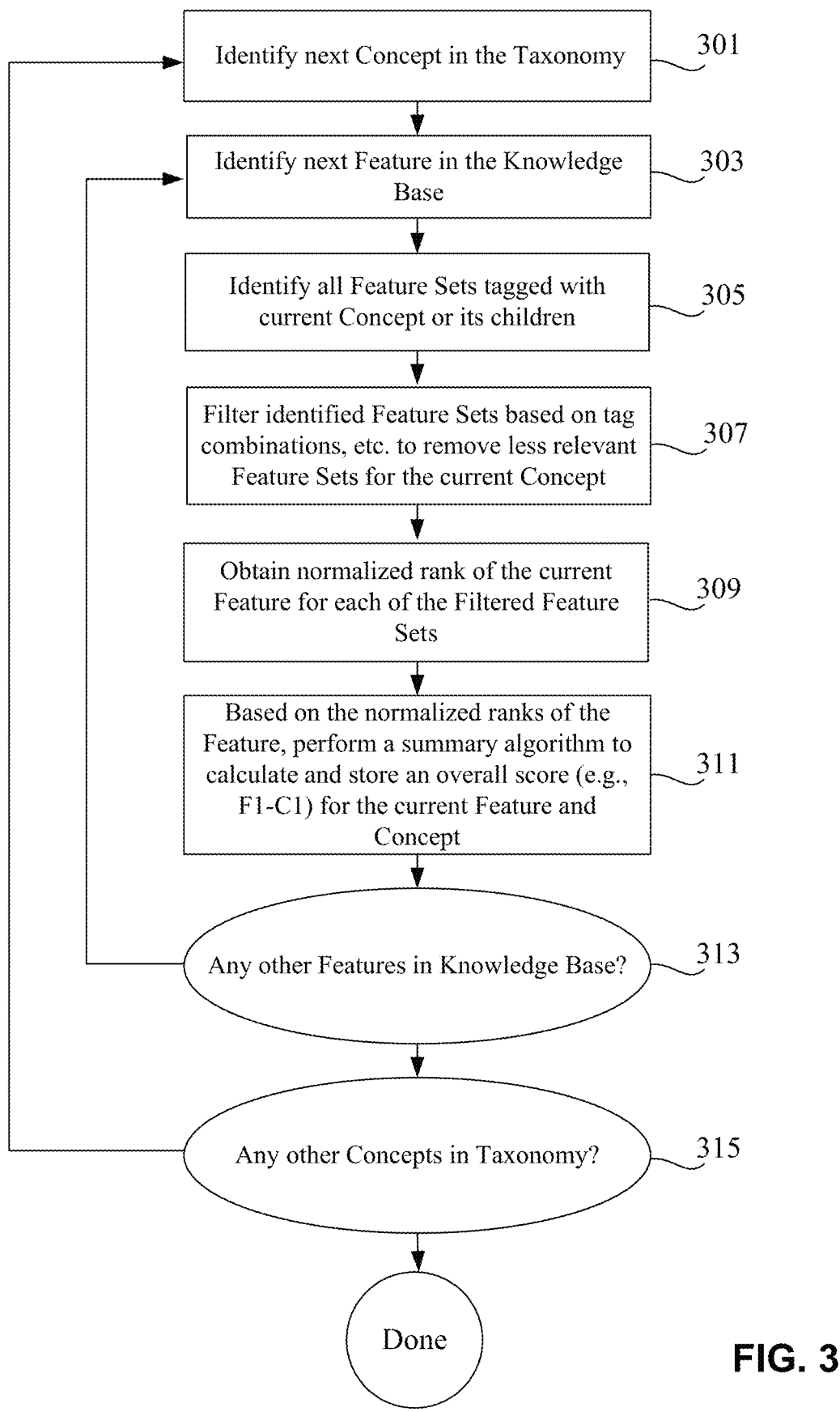
FIG. 3 is a process flow diagram depicting some operations of methods of determining the most relevant concepts for features according to certain embodiments.
Figure 4:
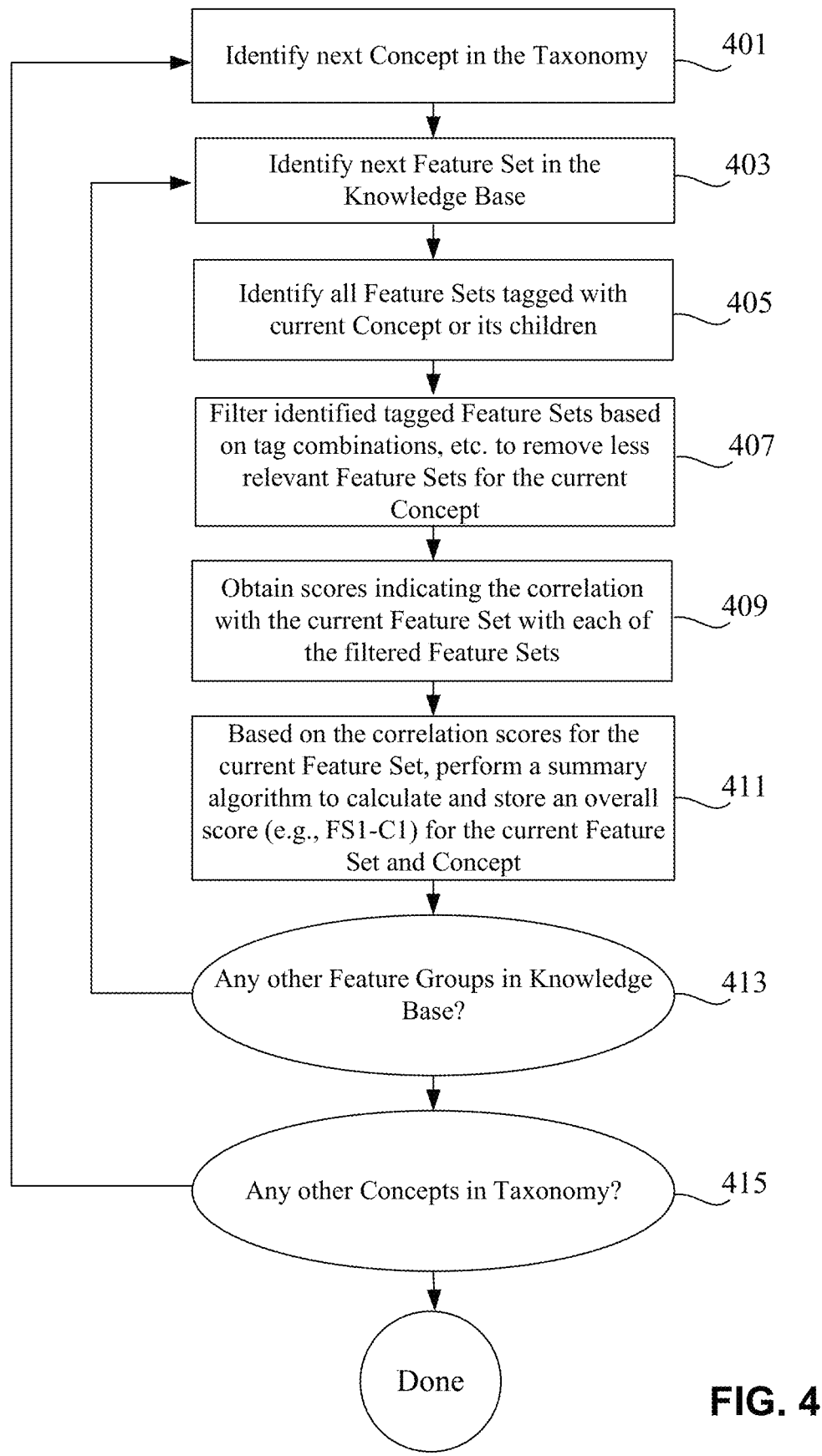
FIG. 4 is a process flow diagram depicting some operations of methods of determining the most relevant concepts for Feature Sets according to certain embodiments.
Figure 5:
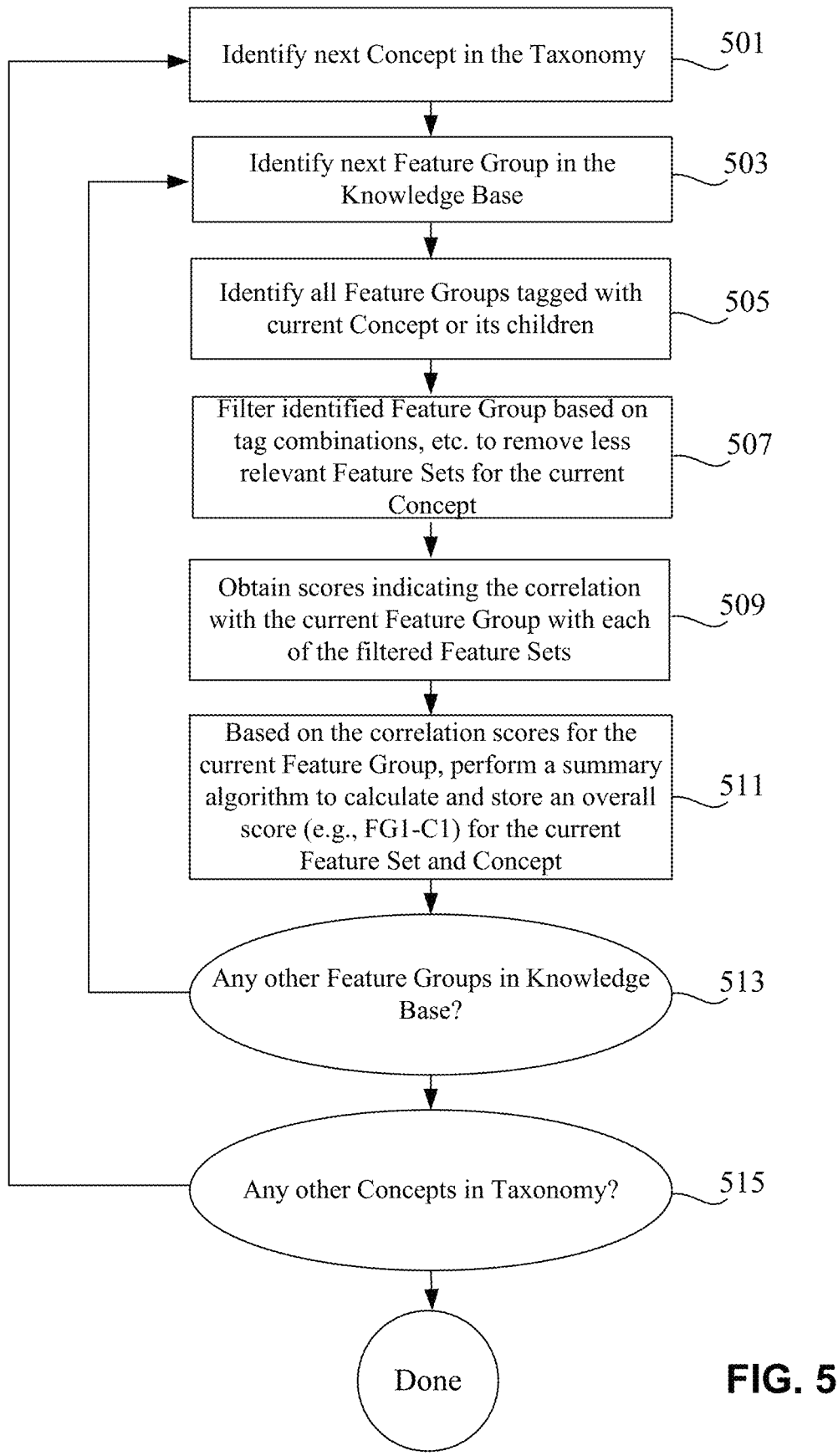
FIG. 5 is a process flow diagram depicting some operations of methods of determining the most relevant concepts for Feature Groups according to certain embodiments.

FIGS. 3-5 are process flow diagrams depicting operations of methods of determining the most relevant concepts for features (FIG. 3), Feature Sets (FIG. 4) and Feature Groups (FIG. 5) according to certain embodiments. These methods may be used, for example, to populate concept scoring tables as represented in FIG. 1, or some other form of storing concept scores. As discussed below, the stored scores may be used for response to user queries about a feature, Feature Set or Feature Group. Although FIGS. 3-5 discuss concept scoring as being performed prior to user queries, so that all Knowledge Base contains information about the most relevant concepts for each feature, Feature Set and Feature Group in the Knowledge Base, it will be apparent that the scoring may also take place on the fly in response to a user query that identifies one or more features, Feature Sets or Feature Groups. Once determined, this information may be stored as indicated in FIG. 1 for use in responding to future queries involving that feature, etc., or discarded.

FIG. 3 depicts a method of determining the relevance of concepts to individual features such as genes, compounds, etc., in accordance with specific embodiments. As depicted, the process begins at an operation 301 where the system identifies a "next" concept in the taxonomy. Typically, the process will consider each concept in the taxonomy. The process next identifies a "next" feature in the Knowledge Base. See block 303. The process typically considers each feature of the Knowledge Base. The process typically determines a score for each possible pair of concept and feature, and so iterates over all possible combinations, as indicated by the two loops in FIG. 3. After setting the concept and feature for the current iteration, the process next identifies all Feature Sets that are tagged with 1) the current concept or 2) its' children concepts. So, for example, referring to FIG. 2, if the concept represented at node 206 is under consideration, all features sets tagged with this concept and/or one or more of the concepts represented at its child nodes 208a, 208b and 208c are identified. In a specific example, a Feature Set tagged only with the concept "stage 2 breast cancer," would be identified for the concept 'stage 2 breast cancer' as well for its' parent concept, "breast cancer."

As discussed further below, the identified Feature Sets are filtered to remove (or in certain embodiments, reweight) Feature Sets that are less relevant to the concept or that would skew the results. After filtering the identified Feature Sets, the normalized rank of the current feature is obtained for each of the filtered Feature Sets, i.e., the Feature Sets remaining after removing the less relevant Feature Sets. See block 309. As described in U.S. Patent Publication 20070162411, features in a Feature Set are typically ranked based on the relative effect on or by the feature in the experiment(s) associated with the Feature Set. See, e.g., the schematic of FIG. 1 in which Feature Set 104 contains rankings of its features. In certain embodiments, obtaining the normalized ranks involves identifying, looking up, or receiving the rank of the feature in each of the filtered Feature Sets. So, for example, for a given feature Fn and a given concept Cm, there may be 25 Feature Sets tagged with Cm and/or at least one of its children concepts. Ten of those twenty-five Feature Sets may contain Fn. The normalized rank of Fn in each of the Feature Sets is obtained: for example, 1/20, null, 4/8, etc., indicating a normalized rank of 1 of 20 features in the first filtered Feature Set, not present in the second Filtered Feature Set, a normalized rank of 4/8 features in the third filtered Feature Set, etc. (These are just examples of normalized ranks: ranks may be normalized using several criteria including Feature Set size, the number of features on a measurement platform for that Feature Set and any other relevant criteria. Use of normalized ranks allows the significance of a feature in one Feature Set to be compared with the significance of that feature in another Feature Set, regardless of the size of the relative size and other differences of the Feature Sets.) After these scores are obtained, an overall score Fn-Cm indicating the relevance of the concept to the feature is obtained. See block 311. In certain embodiments, the criteria used for computation of the final feature-concept score includes the following attributes: normalized rank of that feature in each Feature Set tagged with that concept that passes "inclusion" criteria, the total number of Feature Sets containing this feature that pass the "inclusion" criteria and the total number of Feature Sets tagged with the concept.

The overall score Fn-Cm is then stored, e.g., in a concept scoring table as shown in FIG. 1. Iteration over all features is controlled as indicated at decision block 313 and iteration over all concepts is controlled as indicated at decision block 315. As can be seen, in the method shown in FIG. 3, either iteration can be the inner or outer loop. The method shown in FIG. 3 iterates over all possible combination of concepts in the taxonomy and features in the knowledge base; however, in other embodiments, there may only be a subset of features and/or taxonomy concepts for which a concept score is calculated.

FIG. 4 depicts a method of determining the relevance of concepts to Feature Sets in accordance with specific embodiments. Similarly, to the feature concept scoring, the process begins at an operation 401 where the system identifies a "next" concept in the taxonomy. A "next" Feature Set is also identified at an operation 403. The process typically scores all possible Feature Set—concept pairs. Features Sets tagged with the current concept (and/or its children) are identified and filtered as discussed above with respect to FIG. 3. See blocks 405 and 407. Scores indicating the correlation between the current Feature Set (i.e., the Feature Set identified in operation 403) and each of the tagged and filtered Feature Sets are obtained. See block 409. In many embodiments, these scores are the correlation scores calculated as described in U.S. Patent Publication 20070162411. In many embodiments, they are obtained from a correlation matrix or table scoring such as table 106 depicted in FIG. 1. An overall score FSn-Cm indicating the relevance of the current concept to the current Feature Set is calculated based on the correlation scores obtained in operation 409. In certain embodiments, the criteria used for computation of the final feature set-concept score includes the following attributes: correlation score between Feature Set under study and each Feature Set tagged with a given concept that passes "inclusion" criteria, the total number of Feature sets providing non-zero correlation with the Feature Set of interest that pass the "inclusion" criteria and the total number of Feature Sets tagged with the concept. The overall score may then be stored for use in responding to user queries. The Feature Set and concept iterations are controlled by decision blocks 413 and 415.

FIG. 5 depicts a method of determining the relevance of concepts to Feature Groups in accordance with certain embodiments of the invention. The method mirrors that of concept scoring for Feature Sets depicted in FIG. 4, iterating over Feature Groups instead of Feature Sets. See blocks 501-515. Scores indicating the correlation between the current Feature Group and the filtered Feature Sets may be obtained from a correlation matrix or scoring table as depicted in FIG. 1.

Concept scoring for features, Feature Sets and Feature Groups all involve, for each concept, identifying the Feature Sets that are tagged with the concept and filtering these Feature Sets to remove certain Features Sets that are less relevant to the concept or might skew the results. These operations may be performed for each concept, with the desired feature, Feature Set and/or Feature Group scoring then performed as shown in blocks 309 and 311, 409 and 411, and 509 and 511.

As described above, in certain embodiments, the methods involve filtering the Feature Sets that are tagged with a particular concept to exclude certain Feature Sets. For example, for concepts relating to an organ such as liver, it may be desired to exclude Feature Sets tagged with hepatitis and include only Feature Sets relating to healthy or normal liver tissue. According to various embodiments, the Feature Sets may be filtered based on one or more of the following:

Exclusion of Feature Sets having tags in a particular taxonomy (e.g., excluding all Feature Sets tagged with a Disease from contributing to the concept score of an organ or tissue).

Exclusion of Feature Sets having tags in a particular branch of a given taxonomy or a specific combination of tags Exclusion of certain categories from categorization logic, e.g., because they are too general. For example, a concept such as "Disease" is not particularly useful. A "black list" of such concepts that should not show up in the results may be generated and used to filter out categories.

As described above, in certain embodiments, top level categories include all or some of the following: Diseases, Treatments and Tissues/Organs. An individual Feature Set may have tags from any or all of these categories. As an example, Feature Sets having the following tag combinations may be filtered according to the following logic:

|  | Data Category | | |
| --- | --- | --- | --- |
| Tag Combinations | Diseases | Tissues/Organs | Treatments |
| Diseases | Yes | No | No |
| Diseases + Treatments | Yes | No | Yes |
| Diseases + Tissues | Yes | No | No |
| Diseases + Tissues + Treatments | Yes | No | Yes |
| Tissues | No | Yes | No |
| Tissues + Treatments | No | No | Yes |
| Treatments | No | No | Yes |

The above logic excludes Feature Sets that have tags categorized as either "Disease" or "Treatment" from contributing to the concept score of a tissue/organ. As discussed above, this is so that Feature Sets relating to diseases and/or treatments of these organs do not contribute to the concept score.

The decision logic may be based on the type of experimental data/model under consideration. As noted above, experiments done in cell lines may have little to do with the original disease tissue source for the cell line. Thus, a cell line Feature Set tagged with the original disease concept may skew the statistics with effects unrelated to the disease if allowed to contribute to the concept score of that disease. For example, if there are several hundred biosets (Feature Set) associated with MCF7 breast cancer cells treated with various types of compounds, without filtering these out, there be a significant "bias" when scores are computed for the concept "breast cancer." In this case, filtering the Feature Sets may require excluding certain branches of a taxonomy when a particular disease concepts are scored.

Data Types

The methods, computational systems, and user interfaces described herein may be used with a wide variety of raw data sources and platforms. For example, microarray platforms including RNA and miRNA expression, SNP genotyping, protein expression, protein-DNA interaction and methylation data and amplification/deletion of chromosomal regions platforms may be used in the methods described herein. Microarray generally include hundreds or thousands of different capture agents, including DNA oligonucleotides, miRNAs, proteins, chemical compounds etc., arrayed by affixation to a substrate, localization in nanowells, etc. to assay an analyte solution. Platforms include arrays of DNA oligonucleotides, miRNA (MMChips), antibodies, peptides, aptamers, cell-interacting materials including lipids, antibodies and proteins, chemical compounds, tissues, etc. Further examples of raw data sources include quantitative polymerase chain reaction (QPCR) gene expression platforms, identified novel genetic variants, copy-number variation (CNV) detection platforms, detecting chromosomal aberrations (amplifications/deletions) and whole genome sequencing. QPCR platforms typically include a thermocycler in which nucleotide template, polymerase and other reagents are cycled to amplify DNA or RNA, which is then quantified. Copy number variation can be discovered by techniques including fluorescent in situ hybridization, comparative genomic hybridization, array comparative genomic hybridization, and large-scale SNP genotyping. For example, fluorescent probes and fluorescent microscopes may be employed to detect the presence or absence of specific DNA sequences on chromosomes.

In certain embodiments, high-content and high throughput compound screening data including screening compound effects on cells, screening compound effects on animal tissues and screening interaction between compounds, DNA and proteins, is used in accordance with the methods and systems described herein. High throughput screening uses robots, liquid handling devices and automated processes to conduct millions of biochemical, genetic or pharmacological tests. In certain HTS screenings, compounds in wells on a microtitre plate are filled with an analyte, such as a protein, cells or an embryo. After an incubation periods, measurements are taken across the plates wells to determine the differential impact of the compound on the analyte. The resulting measurements may then be formed into Feature Sets for importation and use in the Knowledge Base. High content screening may use automated digital microscopes in combination with flow cytometers and computer systems to acquire image information and analyze it.

The methods, computational systems, and user interfaces described herein may be used in a variety of research, drug development, pre-clinical and clinical research applications. For example, by querying a concept such as a disease, highly relevant genes and biological pathways may be displayed. Such genes or pathways may in turn be queried against compounds to find possible drug treatment candidates. Without the methods and systems described herein, these research paths are unavailable. Much more complex progressions and connections are enabled as well. Non-limiting examples of such applications include identifying genes linked to a disease, pathways linked to a disease and environmental effects linked to a disease, understanding mechanisms of development and disease progression, studying species diversity and cross-species comparison, identifying novel drug targets, identifying disease and treatment response biomarkers, identifying alternative indications for existing compounds, predicting drug toxicity, identifying a drug's mechanism of action, and identifying amplification or deletion of chromosomal regions.

Additional examples of pre-clinical and clinical research enabled by the methods and systems described herein include absorption, distribution, metabolism and excretion (ADME)—predicting a patient's drug response and drug metabolism, patient stratification into disease categories, e.g., determining more precisely patient stratification a patient's disease stage, identifying early disease biomarkers to enable early disease detection and preventive medicine, and using a patient's genetic profile to estimate the likelihood of disease, drug response or other phenotype. For example, in certain embodiments, a clinician uses a microarray to obtain genetic profile information. The genetic profile information may be imported into the Knowledge Base as a Feature Set. The methods and systems further include instant correlation of that Feature Set to all of the other knowledge in the Knowledge Base, and querying for relevant concepts as described above. Query results may then be navigated and expanded, also as described above.

Multi-Component Framework

Figure 6:
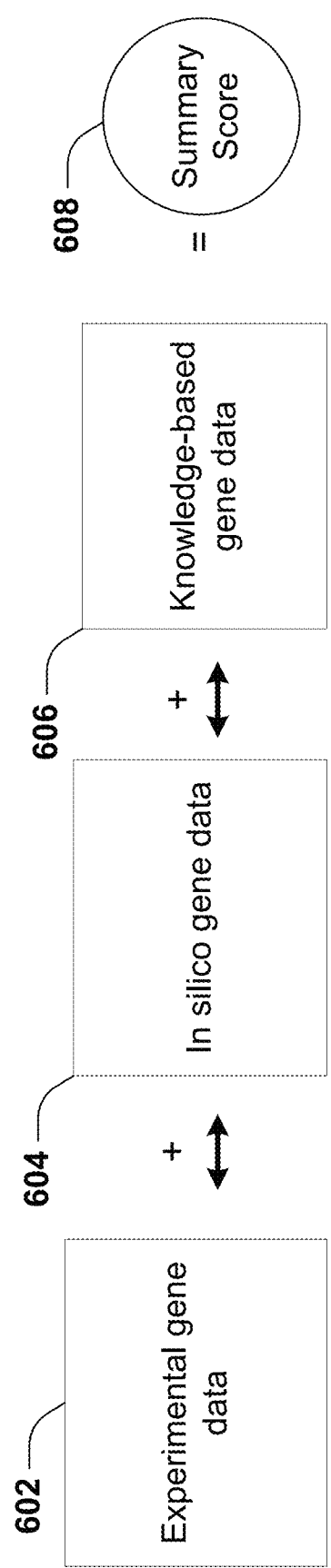
FIG. 6 schematically illustrates an implementation that uses experimental gene data, in silico gene data and knowledge-based gene data to obtain summary scores for genes.

FIG. 6 schematically illustrates an implementation that uses experimental gene data (602), in silico gene data (604) and knowledge-based gene data (606) to obtain summary scores for genes. The summary scores may be used to rank the genes to identify genes that are correlated with or relevant to the concept of interest, such as a phenotype.

In some implementations, the experimental gene data 602 includes gene sets from a database, wherein each gene set of the plurality of gene sets includes a plurality of genes and a plurality of experimental values associated with the plurality of genes. The plurality of experimental values are affected or correlated with the biological, chemical, or medical concept of interest. In some implementations, in silico gene data 604 are obtained from the experimental gene data 602. In some implementations, knowledge-based gene data are obtained from an additional database or an external database separate from the database having experimental gene data. In some implementations, the knowledge-based gene data may be stored in the same database as the experimental gene data. In some in some implementations, the knowledge-based gene data includes gene set data. In some implementations, the knowledge-based gene data 606 includes gene network data. In some implementations, the knowledge-based gene data includes gene group data. A gene group includes a plurality of genes that are associated with each other through various mechanisms such as biological pathway, cell cycle, cell function, cell type, biological activities, common regulation, transcription factor, etc.

FIG. 10 shows a table including illustrative data for the three types of data shown in FIG. 6. Data for 13 hypothetical genes are shown in the table. Each row of the table shows data for a gene. The upper left cell P1 indicates that the data are correlated with a phenotype P1. The three columns with headings S1-S3 show data for three gene sets S1, S2, and S3, which are experimental data. The three columns with headings S1*, S2*, and S3*present in silico gene data derived from the experimental gene data respectfully from gene sets S1, S2, and S3. The column with heading PPI represents interactome data obtained from protein-protein interaction (PPI) network, the PPI data being a form of knowledge-based data.

Another type of knowledge-based data is shown in column with the heading GO, showing gene ontology (GO) data as a form of gene-group data. Experimental data for gene sets S1, S2, and S3 with values above a criterion are delineated in box of 1002. It is worth noting that in silico data for gene set S1*, S2*, and S3*based on the experimental data are obtained for some genes that are beyond the genes having the experimental data in box 1002 for genes 1-9. Namely, data for genes 10 to 13 are obtained and illustrated delineated in box 1004. Knowledge-based data are combined with the experimental data to provide the data in the table.

Similarly for knowledge-based data, data for genes 10, 12, and 13 are obtained, even though the experimental data for those genes are missing or fall below the criterion. As a result, of combining experimental, in silico, and knowledge-based data, summary scores for the genes can be obtained. Because the summary scores take to into consideration information that is above and beyond the experimental data, they are able to better capture information about the genes that are relevant to the phenotype of interest.

The rightmost column indicates the ranks of the summary scores of the 13 genes. Gene 10 has a rank of 9 due to its in silico scores and knowledge-based scores, although it has no experimental score in the table. Some implementations include three components corresponding to the experimental data, the in silico data, and the knowledge based data. The model also includes various parameters corresponding to the three components, as well as other parameters that modify the model to provide more consistent and more valid predictions of gene ranks for the concept of interest. In some implementations, unsupervised machine learning is used to select the parameters of the model reflecting the three component framework. The three component framework and the machine learning techniques for training the model reflecting the framework are further described below.

Figure 7:
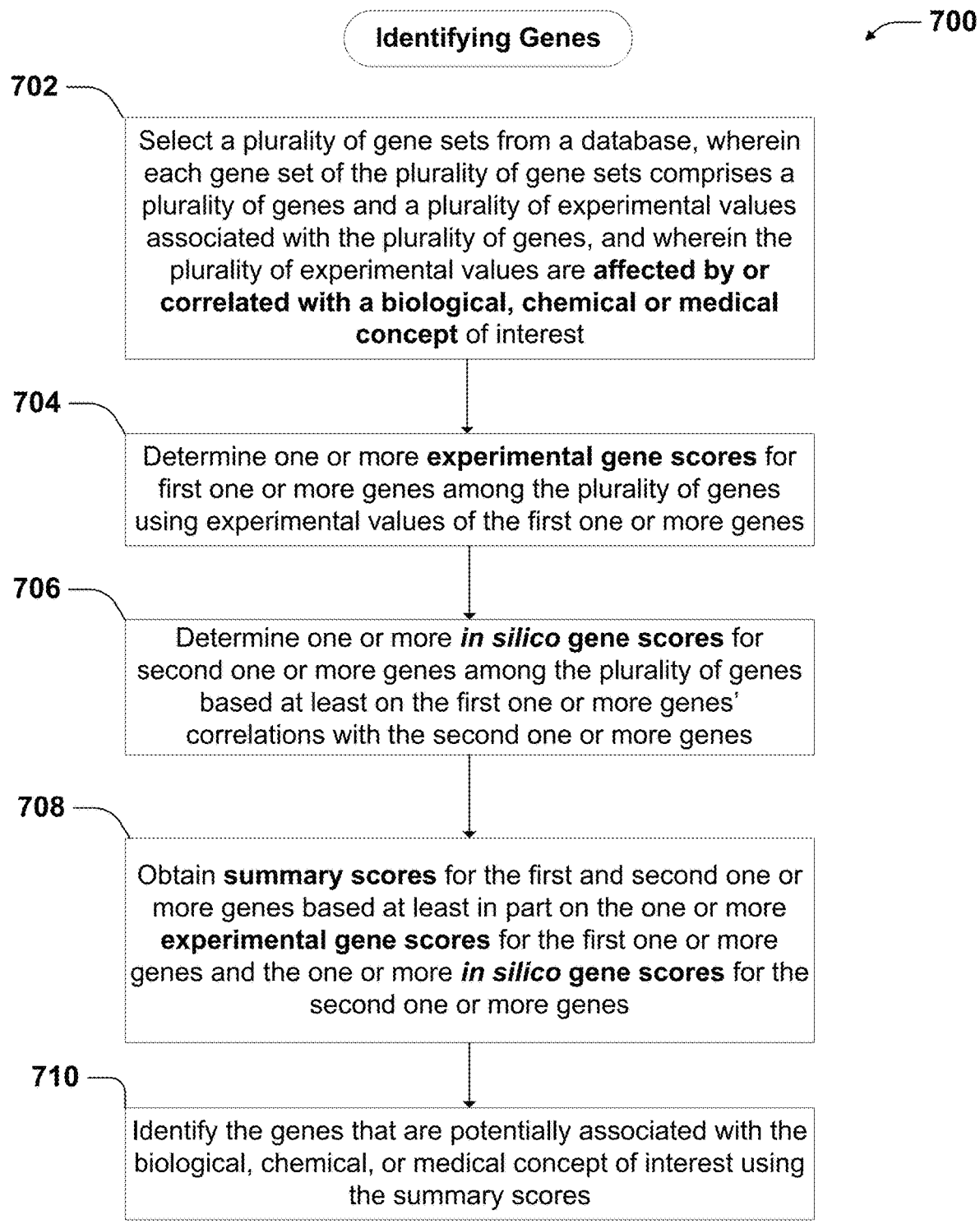
FIG. 7 shows a process for identifying genes that are potentially associated with a biological, chemical, or medical concept of interest according to some implementations.

FIG. 7 shows a process for identifying genes that are potentially associated with a biological, chemical, or medical concept of interest according to some implementations. Process 700 involves selecting a plurality of gene sets from a database, wherein each gene set of the plurality of gene sets includes a plurality of genes and the plurality of experimental values associated with the genes. The plurality of experimental values is correlated with the biological or chemical concept of interest. In some implementations, the plurality of gene sets is tagged by the biological, chemical, or medical concept. In some implementations, the plurality of gene sets is affected by the biological, chemical, or medical concept. In some implementations, a gene set is often related to a single sample for a single study. However, the experimental gene values may also come from different samples or studies in some implementations. In some implementations, the study may compare gene expression levels between normal conditions and disease condition. In some implementations, for instance, a gene set may include data for genes for a disease or data for genes from disease sample with treatment vs. disease sample without treatment.

Process 700 also involves determining one or more experimental gene scores for first one or more genes from the plurality of genes using experimental values of the first one or more genes. FIG. 10 shows schematic data for obtaining gene ranks according to some implementations. Using the example in FIG. 10, three gene sets S1, S2, S3 are selected, and gene scores for the three genes using the experimental values of genes 1-9 in box 1002. In some implementations, the experimental values meet a criterion, such as a lower threshold of 10 (out of 100). In some implementations, the experimental gene scores are normalized so that the top score has a ceiling of 100.

Turning back to FIG. 7, process 700 also involves determining one or more in silico gene scores for second one or more genes among the plurality of genes based at least on the first one or more genes correlations with the second one or more genes. See block 706. In some implementations, the one or more in silico gene scores may be obtained by a process illustrated in FIG. 11.

Process 700 also involves obtaining summary scores for the first and second one or more genes based at least in part on the one or more experimental gene scores for the first one or more genes obtained in 704 and the one or more in silico gene scores for the second one or more genes obtained in 706. See block 708. In some implementations, the summary scores may be obtained by a linear aggregation of the gene scores across the plurality of gene sets. In some implementations, the experimental gene scores and the in silico gene scores are weighted differentially. In some implementations, the summary scores are obtained using a model that receives as inputs experimental scores and in silico scores, and provides as outputs summary scores for the genes. In some implementations, process 800 shown in FIG. 8 may be used to obtain the summary scores.

Process 700 further involves identifying the genes that are potentially associated with the biological, chemical, or medical concept of interest using the summary scores. See block 710. In some implementations, the summary scores may be normalized. In some implementations, the summary scores may be used to rank the genes, and the highly ranked genes may provide candidates to a gene panel. In some implementations, the identified genes for a phenotype may be used to inform the process of obtaining genes for a related phenotype such as when the two phenotypes have a genus-species relation. In some implementations, the genes selected for the two related phenotypes may be compared to provide higher order information, such as identifying common underlying mechanism of the two phenotypes.

Figure 8:
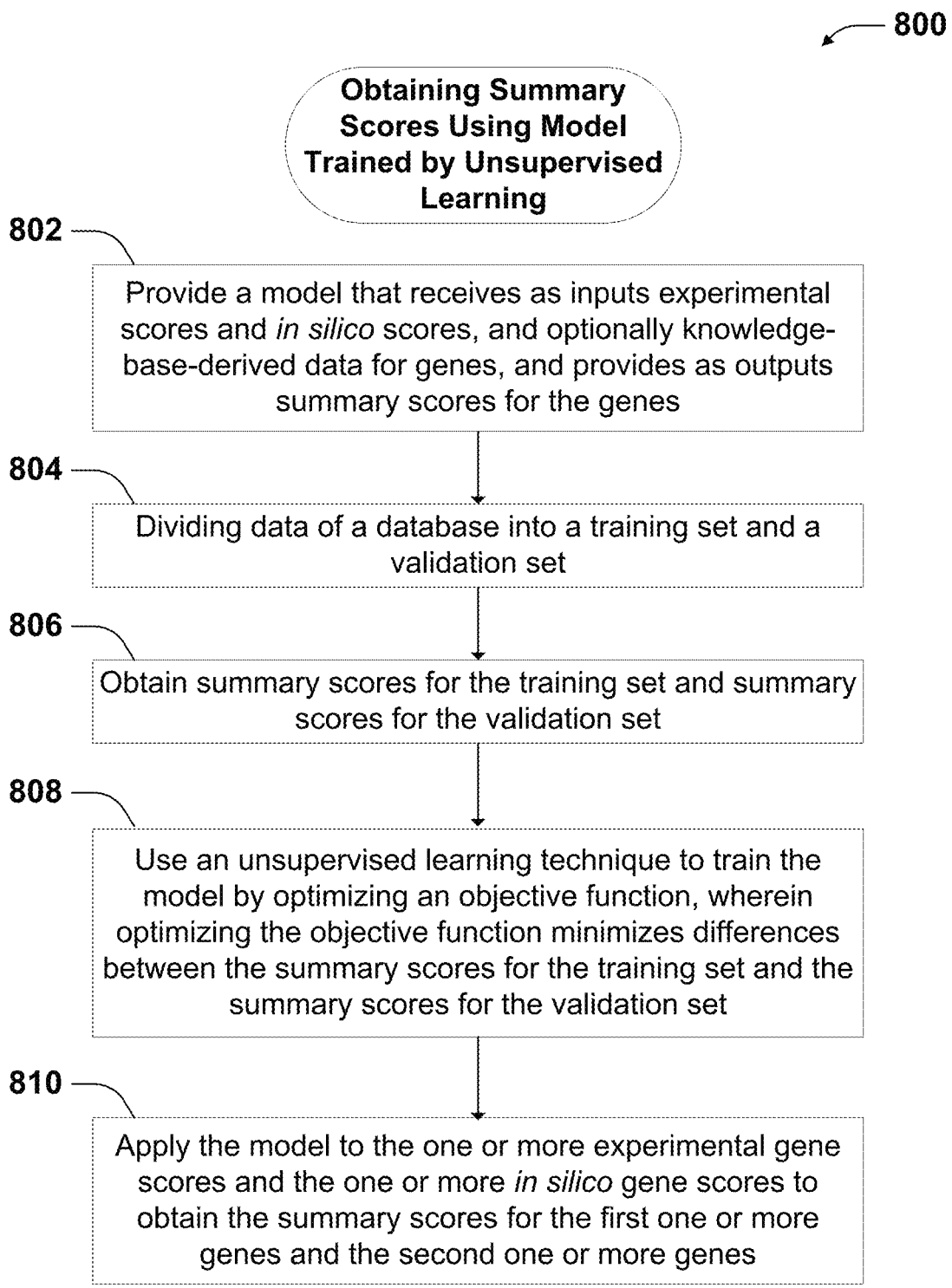
FIG. 8 shows a process for obtaining summary scores using a model trained by unsupervised learning.

FIG. 8 shows a process (800) for obtaining summary scores using a model trained by unsupervised learning. Process 800 involves providing a model that receives as inputs experimental scores and in silico scores. The model also provides as outputs summary scores for the genes being tested. See block 802. Process 800 further involves dividing data of a database into a training set and a validation set. See block 804. Process 800 then involves obtaining summary scores for the training set and summary scores for the validation set. See block 806. Process 800 further involves using an unsupervised learning technique to train the model by optimizing an objective function. In some implementations, optimizing the objective function comprises minimizing differences between the summary scores for the training set and the summary scores for the validation set. In some implementations, process 800 further involves applying the trained model to the one or more experimental gene scores in the one or more in silico gene scores to obtain the summary scores for the first one or more genes and the second one or more genes.

In some implementations, the summary scores are normalized. In some implementations, each summary score is aggregated by means of linear combination of singular values. In some implementations, the linear combination involves a sum of squares. In some implementations, the first one or more genes are not identical to the second one or more genes.

In some implementations, the model has the form:

$$F(\theta)=k1*c1+k2*c2+ \ldots +kn*cn$$

wherein θ are parameters of the model, ci are components of the model, and ki are weight factors for the components.

In some implementations, the method further comprises partitioning one or more of the components of the model into subcomponents based on the sample weights of experimental data types. For instance, the experimental data can include RNA expression data, DNA methylation data, and SNP data as component C1. The model can partition the weight of K1 to the three experimental types, providing e.g., 0.7 to RNA expression data, 0.2 to DNA methylation data, and 0.1 to SNP data.

In some implementations, optimizing the objective function includes minimizing differences between the summary scores for the training set and the summary scores for the validation set. In some implementations, in optimizing the objective function, summary scores are ranked and binned in buckets of a defined size. Penalty scores are assigned to the buckets, the penalty scores favoring higher rank summary scores. FIG. 9 shows data for illustrating optimizing the objective function. The first column from the left shows the ranks of 20 genes obtained from a test data set based on the summary scores for the test data set. The second column from the left shows the summary scores for the rank genes. The third column from the lest shows data for the summary scores for the validation set. In some implementations, an objective function minimizes the score differences between the test set and the validation set. For instance, a root mean square difference can be minimized when optimizing the objective function.

In some implementations, the summary scores are binned into buckets of a particular size. As shown in FIG. 9, bucket #1 includes genes ranked 1-5, to which a penalty weight of 1 is assigned. The penalty weight is multiplied by the gene summary scores. Therefore, genes ranked 1-5 are not penalized. Genes that are ranked from 6 to 10 are binned in bucket #2 and assigned the penalty score of 0.95. Genes ranked number 11 to 15 are assigned to bucket #3 and assigned a penalty score of 0.9. Finally, genes ranked 16 to 20 are placed in bucket #4 and assigned a penalty score of 0.85. Therefore, genes that are ranked higher are penalized less or weighted more heavily in the optimization process of block 808. In some implementations, the objective function is based only on top ranked summary scores, where lower ranked genes have a penalty score of zero.

In some implementations, rank difference in buckets ordinal number instead of individual gene ranks may be used as an objective function for more coarse comparison, which may smooth out noise in some implementations.

In some implementations, different buckets size may be applied to a model to evaluate the model's predictive power. If a model performs well with a small bucket size, it indicates that the model has good predictive power.

In some implementations, the method comprises training the model by optimizing an objective function. In some implementations, training the model comprises applying a bootstrap technique to bootstrap samples. In some implementations, the objective function relates to at least one summary score distribution after bootstrapping. In some implementations, optimizing the objective function comprises maximizing the distance between a summary score distribution obtained from concept specific gene sets and a summary score distribution obtained from random gene sets.

Biotag-Based Gene Set Prioritization

In some implementations, different studies include different quantities and properties of gene sets. Some implementations provide mechanisms to select the appropriate gene sets from studies. For example, the first study has 30 gene sets of perturbation data. A second study has three gene sets of perturbation patient data. A third study has three different drug treatments of a disease. A fourth study includes data from 20 different concentrations of the same compound. Some implementations of the disclosure provide mechanisms to select gene sets from the studies so the different studies have similar influence for the overall scores of the genes. Some implementations solve the problem using priority biotag of studies. In some implementations, gene set data are tagged with different biotags to indicate the properties and nature of the data in the gene set. Different weights are then assigned to the biotags. In an all gene sets can provide composite biotech scores each i If genes associated with two or more tags, a composite biotag score may be obtained from the biotags. Biotag categories include but are not limited to tissue types, bio design, by group, bio source, compound, gene mode, etc. Examples of the tags in the different categories are provided below.

Biosource: required to describe how a sample was derived. It includes cell lines compiled from resources such as ATCC, HPA, Tumorscape, DSMZ, hESCreg, ISCR, JCRB, CellBank Australia, COSMIC, NIH Human Embryonic Stem Cell Registry, RIKEN BRC.

Biodesign: required to describe the nature of the comparison. Tag the biodesign(s) that most describe the driving difference(s) in the bioset.

Tissue: required to define the specific organ/tissue/cell type. Tissue ontologies are derived from MeSH.

Disease: assigned only if a sample corresponds to a disease state. Disease ontologies are derived from SNOMED CT.

Compound: a sample was affected by a compound. Compound ontologies are derived from MeSH.

Gene: a gene in a sample was modified or served as the key differentiating marker between experimental groups (e.g. ER− vs. ER+ breast cancer). Sources include NCBI's Entrez Gene, Unigene, and GenBank, EMBL-EBI Ensembl, and others.

Genemode: describe a gene modification. Genemode cannot be assigned without being linked to a specific gene.

Biogroup: used as tags when no other vocabulary above provides relevant terminology. Biogroups are derived from resources such as MSigDB, GO, EMBL-EBI InterPro, PMAP, TargetScan.

| Genemode |
|---|
| Cell marker |
| Negative |
| Positive |
| Gene overexpression |
| Conditional |
| Constitutive |
| Ectopic |
| Epigenetic |
| Knock-in |

Mimic overexpression
Gene knockdown
Epigenetic
Morpholino
RNA interference
shRNA knockdown
siRNA knockdown
ncRNA knockdown
miRNA knockdown
Gene knockout
Conditional
Irreversible
Gene mutation
Amplification
Deletion
Fusion
Insertion
Inversion
Translocation
Amorphic
Neomorphic
Hypermorphic
Hypomorphic
Antimorphic—Dominant-negative
Immunoprecipitation—co-IP
ChIP antibody target
RIP antibody target
Protein treatment
Antibody target—inhibitory
Antibody target—stimulatory Biodesign Clinical
Clinical study—Clinical outcome
Data validation
Below threshold significance
Insufficient replicates
Insufficient sequence reads
Demographic comparison
Age comparison
Gender comparison
Ethnicity comparison
Disease comparison
Disease vs. normal
Disease vs. disease
Disease resistant vs. sensitive
Genetic perturbation
Mutant vs. wildtype
Mutant vs. mutant
Growth conditions
Environmental conditions
Compound withdrawal
Treatment deprivation
Pharmacological response
Response to a drug—Drug non-response vs. complete response—Drug non-response vs. partial response—Drug partial vs. complete response
Drug resistant vs. sensitive
Timecourse
Circadian time course
Developmental time course
Treatment time course
Treatment comparison
Dose response
Treatment vs. control
Treatment vs. treatment
Other comparison types
Biomarker comparison
Biosource comparison
Method comparison
Normal vs. normal
Quantitative trait analysis
Species comparison
Strain comparison Biosource Blood fraction
Bone marrow fraction
Cell line (specific if available)
Cell lysate
Primary cells
Primary cells—cultured
Primary cells—laser capture
Primary tissue—FFPE (formalin-fixed, paraffin-embedded)
Primary tissue—fresh or fresh frozen
Whole blood
Whole body
Whole organ
Xenograft In some implementations, gene sets are selected based on one or more biotags associated with the gene sets. In some implementations, the gene sets having the highest biotag scores are selected in the analysis, while the unselected genes are excluded from the downstream analysis. In some implementations, a study is excluded if the number of genes in the study is below the first criterion. In some implementations, the top ranked genes as in terms of biotag scores are selected, with the number of selected gene sets not exceeding a second criterion.

In some implementations, biotags are used to filter out gene sets. For example, a biotag of the gene set may indicate that the gene set is tagged with a knockdown of a specific gene that is irrelevant to the phenotype of interest. The experimental values of the genes in the gene set are likely regulated by the knockdown gene rather than the genotype of interest. Given this information, therefore, the gene set is removed from analysis in some implementations to avoid compounding effect from the knockdown gene.

In Silico Gene Scores

Implementations of the disclosure provide methods and systems for obtaining in silico gene scores from experimental gene scores. In various implementations, the identified in silico data are correlated with the experimental data, but are not completely parallel.

Figure 11:
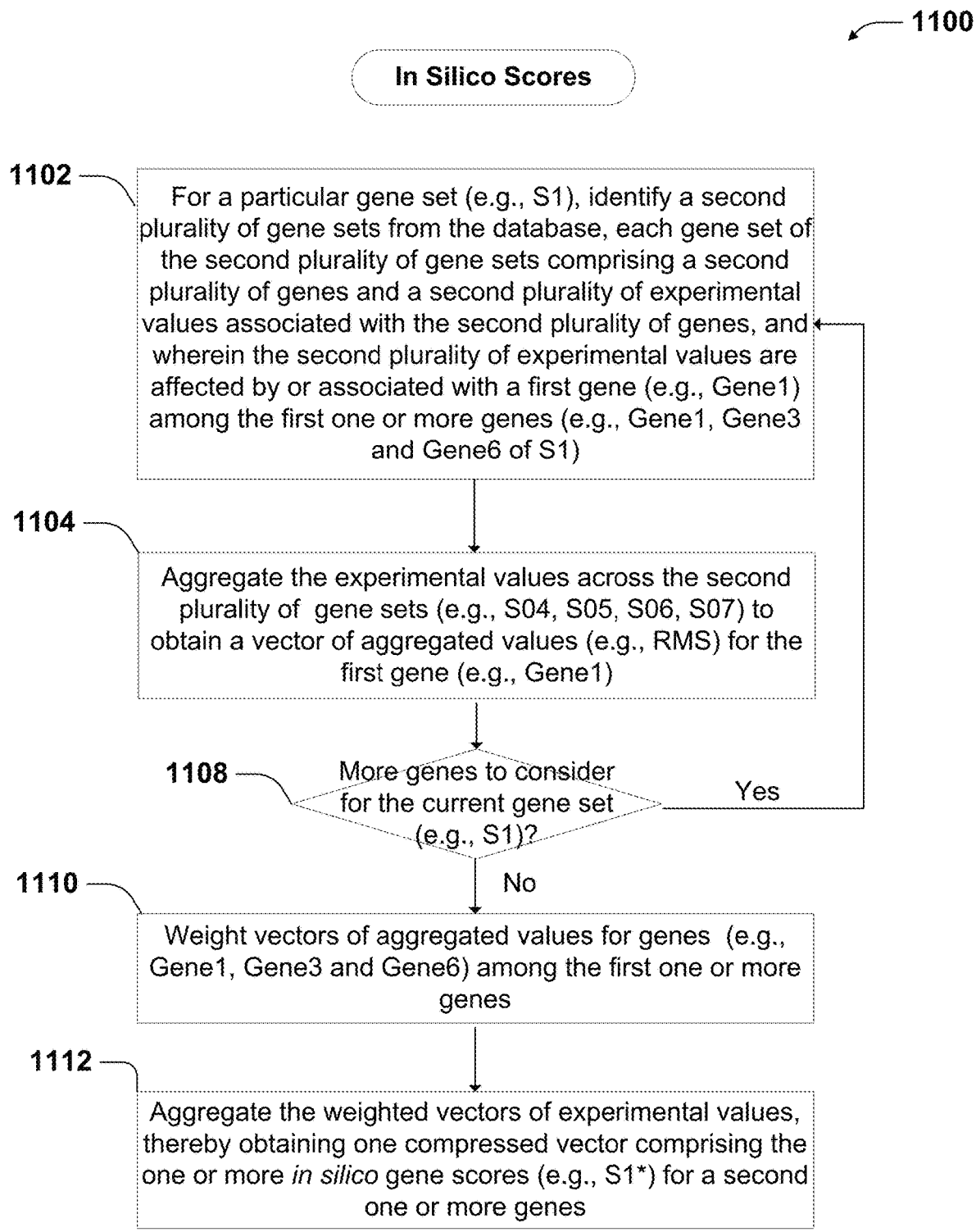
FIG. 11 shows a process for obtaining in silico scores from experimental gene set data.

FIG. 11 shows a process 1100 for obtaining in silico scores from experimental gene set data. Referring back to the illustrative data in FIG. 10, in silico gene set data S1* is obtained for experimental gene set S1. Similarly, in silico gene set data can be obtained for other empirical experimental gene sets, respectively. In FIG. 11, process 1100 involves identifying, for the for particular gene set (e.g., S1 in FIG. 10) the second plurality of gene sets from the database, each gene set of the second plurality of gene sets comprising a second plurality of genes and the second plurality of experimental values associated with the second plurality of genes. The second plurality of experimental values are associated with the first gene (e.g., Gene 1 in FIG. 10) among the first one or more genes (e.g., Gene 1, Gene 3, and Gene 6 of S1 in FIG. 10).

In some implementations, process 1100 involves aggregating the experimental values across the second plurality of genes to obtain a vector of aggregated values for the first gene. Process 1100 then checks to see whether more genes need to be considered for the current gene set. If so, it returns to step 1102 to identify another plurality of gene sets from the database to obtain a vector of aggregated values for the instant gene. If no more genes need to be considered for in silico scores, the aggregated vectors for the genes are weighted in some implementations. See block 1110. Process 1100 then aggregates the weighted vectors of experimental values to obtain a compressed vector comprising the one or more in silico gene scores for the second one or more genes.

FIG. 12 shows illustrative data for a gene set S1 correlated with phenotype P1. See block 201. FIG. 12 also shows how in silico data may be obtained from the experimental data of gene set S1 of 1202. In some implementations, a first gene, Gene 1, having the highest experimental score of 92 is selected to generate n matrix of data in box 1204. Matrix 1204 includes gene sets that are identified to be correlated with Gene 1. In other words, one or more experimental values of the genes in gene sets S04-S07 are correlated with Gene 1. Similarly, gene sets are identified for Gene 3, to provide the matrix data in box 1206. Again, gene sets S08-S10 correlated with gene three. Similarly, gene sets S11-S15 are selected or identified. See block 1208. For each of the matrices 1204, 1206, and 1208, the experimental values of the genes are aggregated across the gene sets in the matrix to obtain an aggregated vector of gene scores that are indicative of correlations between the particular gene and other genes across the identified gene sets.

In some implementations, the experimental gene scores are aggregated by linear aggregation. In some implementations, the aggregated genes comprise root mean squares of the experimental scores. Then the aggregated vectors of the three genes are further aggregated in matrix 1210 to provide a compressed vector S1*. The resulting S1* vector reflects the correlation of other genes in other gene sets with the three genes in gene set S1. In some implementations, each of the aggregated vectors, Gene 1 RMS, Gene 3 RMS, and Gene 6 RMS, is weighted in proportion to an experimental value of the corresponding gene in the gene set S1. In other words, the weights for, Gene 1, Gene 3, and Gene 6 in matrix 1210 are weighted proportional to 92, 63, and 32.

In some implementations, each of the aggregated vectors for particular gene is weighted in proportion to the number of gene sets of the second plurality of gene sets identified for the particular gene. In other words, because matrix 1204 has 4 gene sets, matrix 1206 has 3 gene sets, and matrix 1208 has a 5 gene sets, the three genes in matrix 1210 are weighted proportional to 4, 3, and 5. In some implementations, the gene scores for S1 in matrix 1210 can be normalized to a range between 0-1, which can be used as a weight factor for the vectors in matrix 1210.

With the in silico gene scores and the experimental gene scores obtained using the methods described above, data can be provided to the model described above to determine summary scores for the first and second one or more genes. If the correlations are strong among many gene, the model term relating to the in silico gene scores will be large. Conversely, if the correlations among the genes are small, the in silico gene score term will be small. In the latter case, fewer genes in the experimental gene sets need to be processed to obtain the in silico gene scores in some implementations.

Gene-Group Data

In some implementations, gene set theory data may be synergistically combined with experimental gene data to determine summary scores for ranking genes associated with the concept of interest. In some implementations, gene-group scores are computed in addition to experimental gene scores and in silico gene scores.

In some implementations, the method includes determining one or more gene group scores for third one or more genes. In some implementations, the method comprises obtaining the summary scores for the first and second one or more genes based at least in part on the gene-group scores for at least some of the third one or more genes, as well as the one or more experimental scores for the first one or more genes determined in (b) and the one or more in silico scores for the second one or more genes determined in (c). In some implementations, the plurality of genes related to a label comprises genes in a gene set library. In some implementations, the genes in the gene set library comprise genes in a gene ontology.

Figure 13:
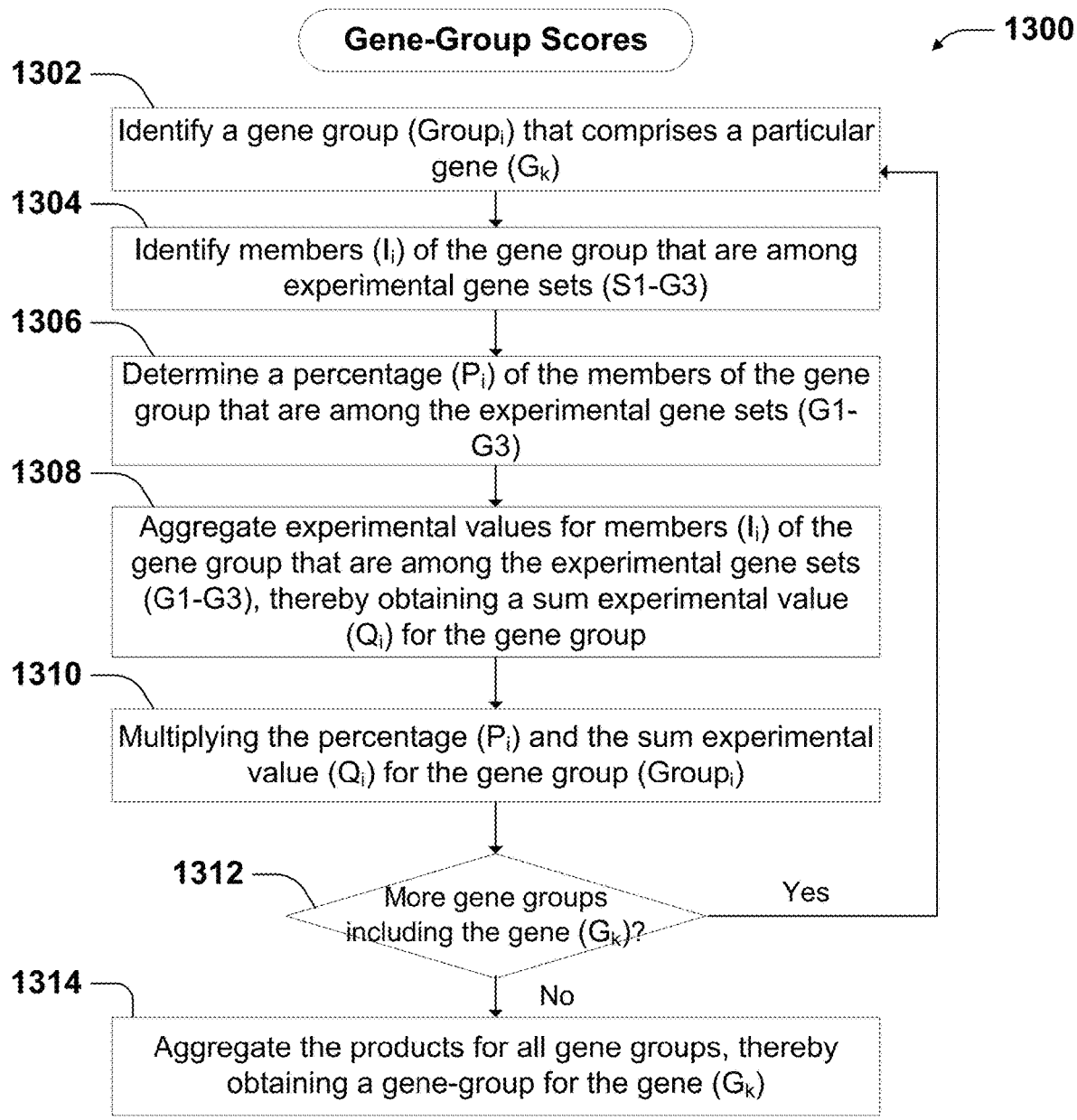
FIG. 13 shows a process through which the gene-group scores may be obtained according to some implementations.

FIG. 13 shows a process through which the gene-group scores may be obtained according to some implementations. Process 1300 involves identifying a gene group that comprises the particular gene for which the gene score is to be calculated. See block 1302.

Figure 14:
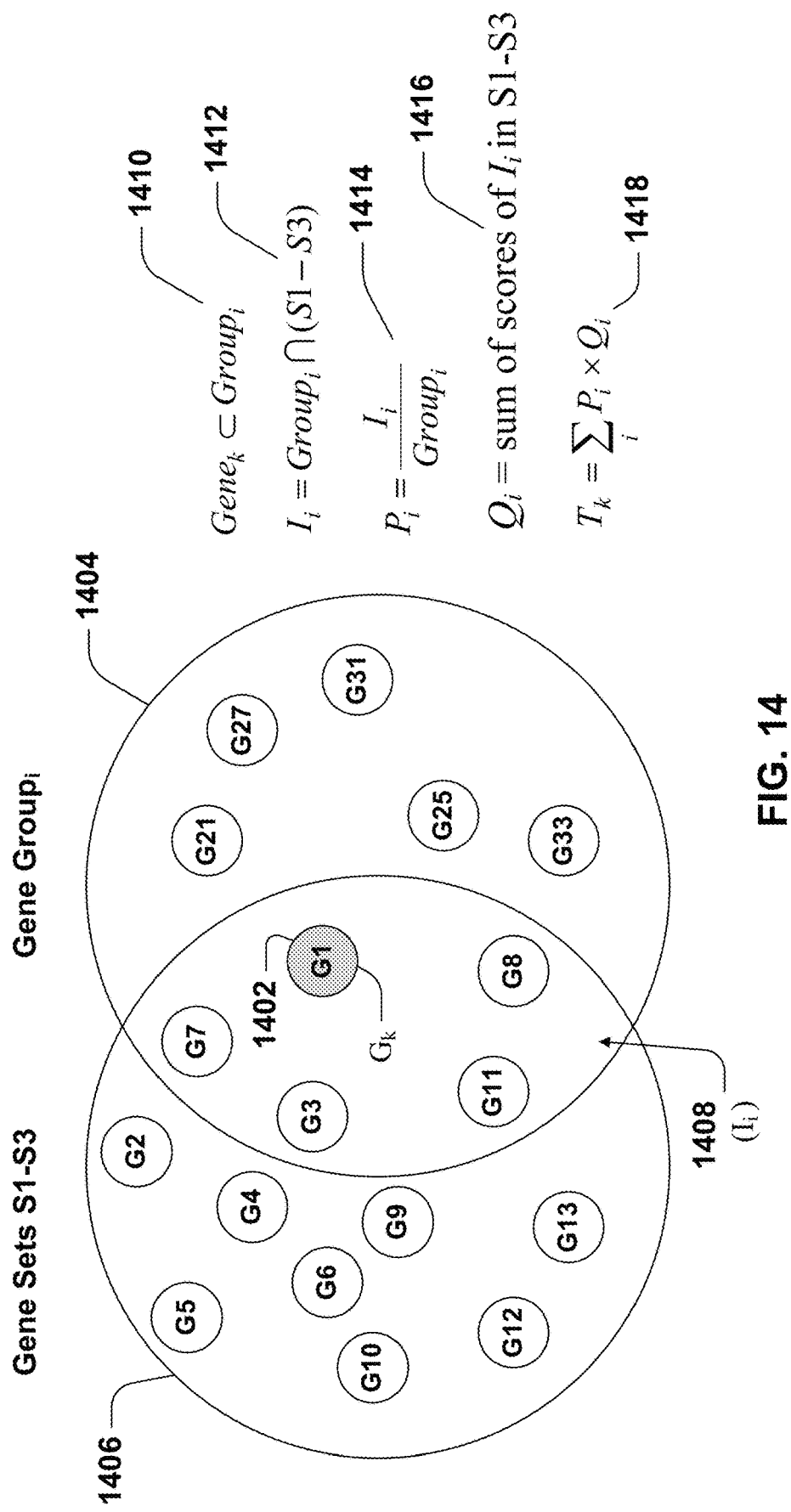
FIG. 14 shows an illustrative diagram of the genes of gene sets S1-S3 and the genes of gene group.

The data illustrated in FIG. 14 are used to help illustrate the process 1300 in FIG. 13. And they are not intended to limit the scope of process 1300 to the example of FIG. 14. FIG. 14 shows an illustrative diagram of the genes of gene sets S1-S3 and the genes of gene group. It also illustrates how gene-group scores may be obtained from the data. Set 1406 includes genes from gene sets S1 to S3. The instant gene of interest for which a gene-group score is to be calculated is G1 (1402). The set 1404 indicates Gene Group$_i$. The intersection of set 1406 and set 1404 is 1408 ($I_i$).

Step 1302 of process 1300 of FIG. 13 identifies a gene group (Group$_i$) that comprises a particular gene (G$_k$). See equation 1410. Process 1300 further involves identifying members ($I_i$) of the gene group that are among experimental gene sets (S1-S3). See block 1304 and equation 1412. In some implementations, genes in the gene group comprise genes in a gene set library. In some implementations, the genes in the gene set library comprise genes in a gene ontology. In some implementations, a label of the gene group indicates a biological function, a biological pathway, a common feature, etc.

Process 300 further involves determining the percentage (e.g., P$_i$ in FIG. 14) of the members of the gene group (Group, of FIG. 14) that are among the experimental gene sets (G1-G3 of FIG. 14) see block. See equation 1414. Process 1300 further involves aggregating experimental values for members ($I_i$ of FIG. 14) of the gene group that are among the experimental gene sets, thereby obtaining a sum experimental value (Q$_i$) for the gene group. See block 1308 and equation 1416.

FIG. 15 illustrates the experimental values for members $I_i$ of the gene group that are among the experimental gene sets (G1 to G3), which are shown as shaded cells surrounded by box 1002 in FIG. 15. Here, the members in the intersection $I_i$ include genes G1, G3, G7, G8, and G11. Therefore, the corresponding experimental values for the above genes in gene sets S1, S2, and S3 as highlighted are summed to provide the sum experimental value (S$_i$) for the gene group.

Process 1300 further involves multiplying the percentage (P$_i$) and the sum experimental values (Q$_i$) for the gene group (Group). See equation 1418 of FIG. 14 and block 1310 of FIG. 13. Process 1300 further involves determining if there are more gene groups that includes the instant gene. See block 1312. If so, the process returns to block 1302. If not, process 1300 continues to block 1314 to aggregate the products for all gene groups, thereby obtaining a summary score (T$_k$) for the instant gene as:

$$T_k = \sum_i P_i \times Q_i$$

Interactome Data

In some implementations, interactome data are integrated in the processing framework to determine the summary scores for the genes.

In some implementations, the methods further comprise determining interactome scores respectively for fourth one or more genes. In some implementations, each interactome score for the particular gene is determined using (1) connections between the particular gene and other genes connected to the particular gene in a network of genes and (2) at least some of the one or more experimental values of the first one or more genes. In some implementations, the method comprises obtaining the summary scores for at least the first one or more genes and the second one or more genes based at least in part on the interactome scores for at least some of the fourth one or more genes, as well as the one or more experimental gene scores for the first one or more genes determined in (b) and the one or more in silico gene scores for the second one or more genes determined in (c). In some implementations, the network of genes are based on interactions and/or relations among genes, proteins, and phospholipids.

Figure 16:
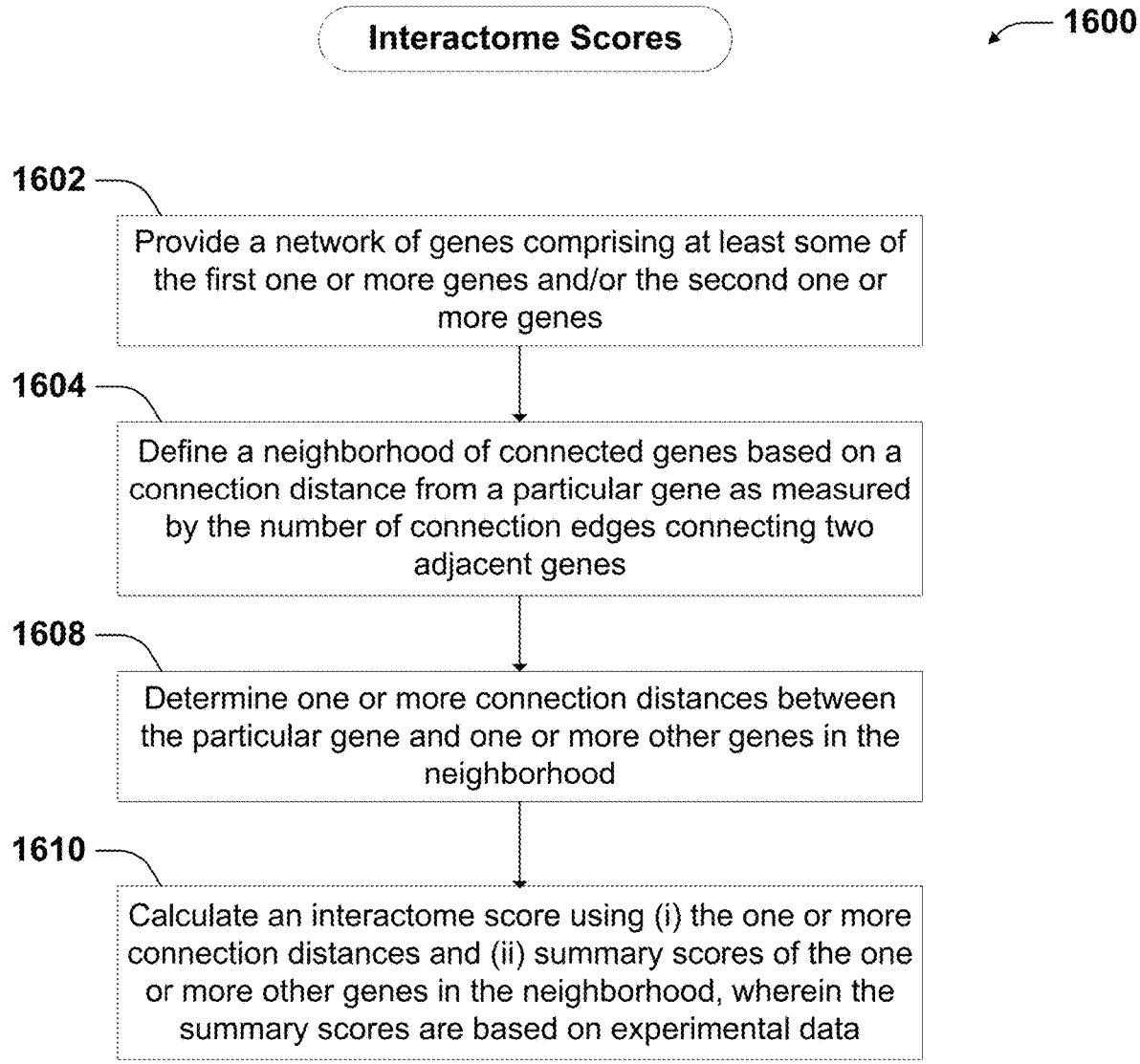
FIG. 16 illustrates a process for calculating interactome scores according to some implementations.

Some implementations of the disclosure provide methods for calculating interactome scores using knowledge-based data and experimental data. FIG. 16 illustrates a process for calculating interactome scores according to some implementations. Process 1600 involves providing a network of genes comprising at least some of the first one or more genes and/or the second one or more genes. The first one or more genes relate to experimental gene data, and the second one or more genes relate to in silico gene data. Each pair of genes in the network are connected by an edge. The genes of the network comprise the fourth one or more genes.

Figure 17:
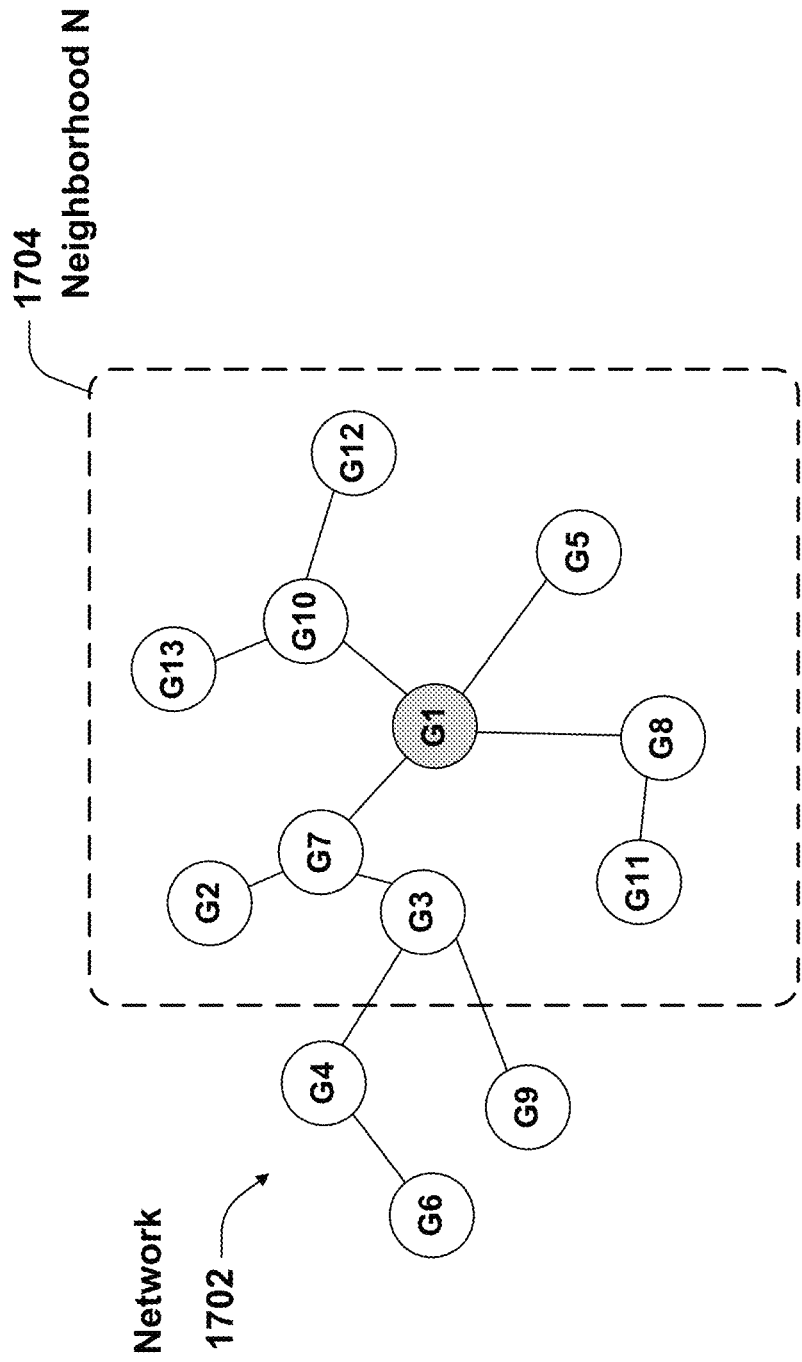
FIG. 17 shows a diagram illustrating how interactome data may be obtained for a network of genes.

FIG. 17 shows a diagram illustrating how interactome data may be obtained for a network of genes 1702 including genes G1-G13. The network 1702 is an example of a network that can be provided in step 1602. Process 1600 further comprises defining a neighborhood of connected genes for a particular gene based on a connection distance from the particular gene as measured by the number of connection edges. See block 1604. The neighborhood 1704 is an example of the neighborhood defined in 1604. The neighborhood 1704 includes genes that have a connection distance from gene G1 of two or fewer connection edges.

Process 1600 further involves determining one or more connection distances between the particular gene (G1) and one or more other genes in the neighborhood. See block 1608. Process 1600 further involves calculating interactome score using (i) the one or more connection distances and (ii) summary scores of the one or more other genes in the neighborhood, wherein the summary scores are based on experimental data.

Figure 18:
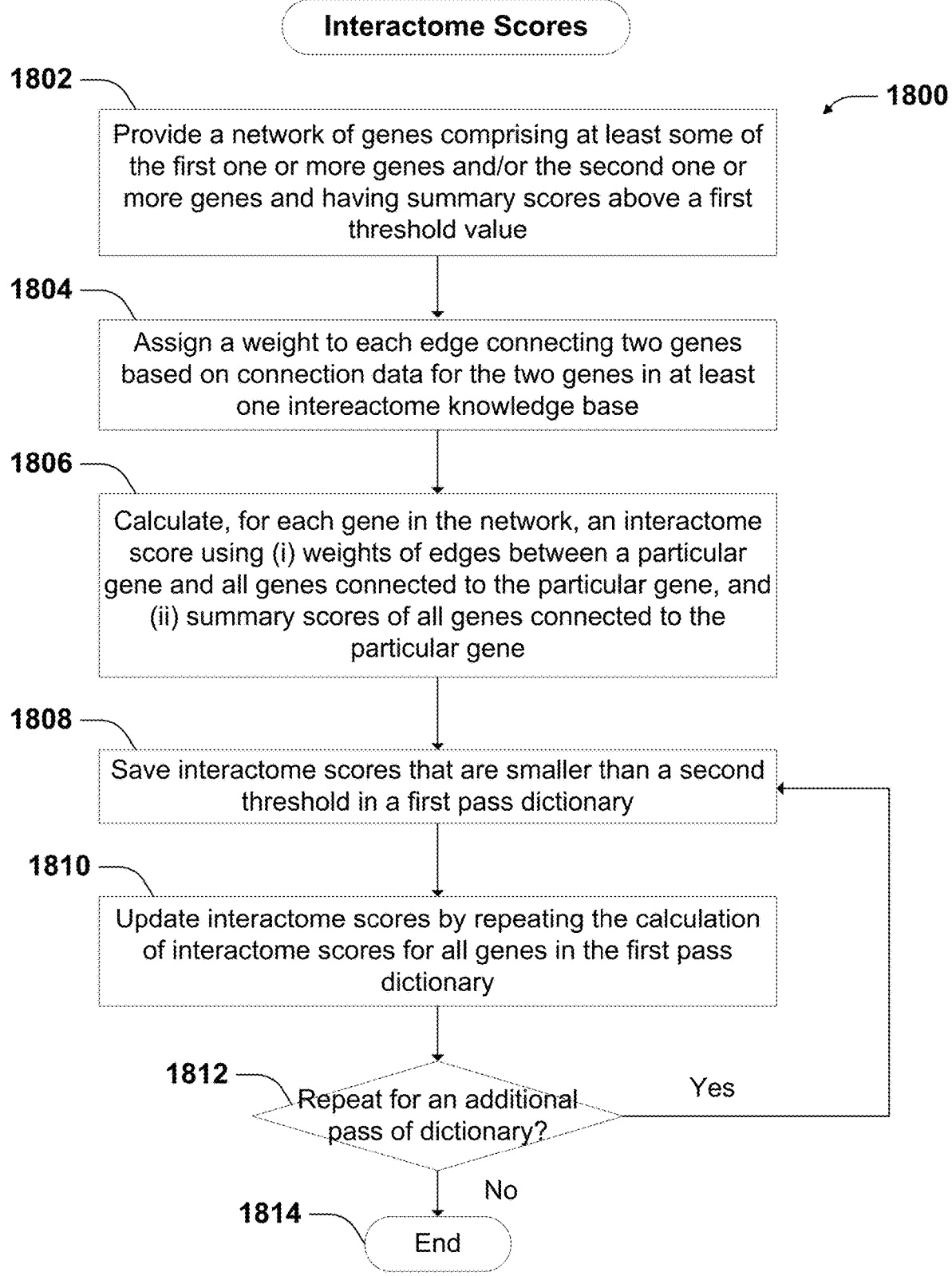
FIG. 18 shows a process according to another implementation for obtaining interactome scores using interactome data and experimental data.

In some implementations, the interactome score is calculated as proportional to a sum of multiple fractions, each fraction being a summary score of another gene in the neighborhood divided by a connection distance between the particular gene and the other gene in the neighborhood. In some implementations, the interactome score for gene Gk is estimated as:

$$Interactome\_G_k \sim \Sigma(SG_i/dG_i)$$

where $G_i \cap N$, $dG_i$ is distance of $G_i$ to $G_k$ and $SG_i$ is an experiment-based summary score for $G_i$ In some alternative implementations, interactome scores may be determined using process 1800. FIG. 18 shows process 1800 as an alternative implementation for obtaining interactome scores using interactome data and experimental data. Process 1800 involves providing a network of genes comprising at least some of the first one or more genes and/or the second one or more genes. The genes in the network have summary scores above a first threshold value. See block 1802.

Figure 19:
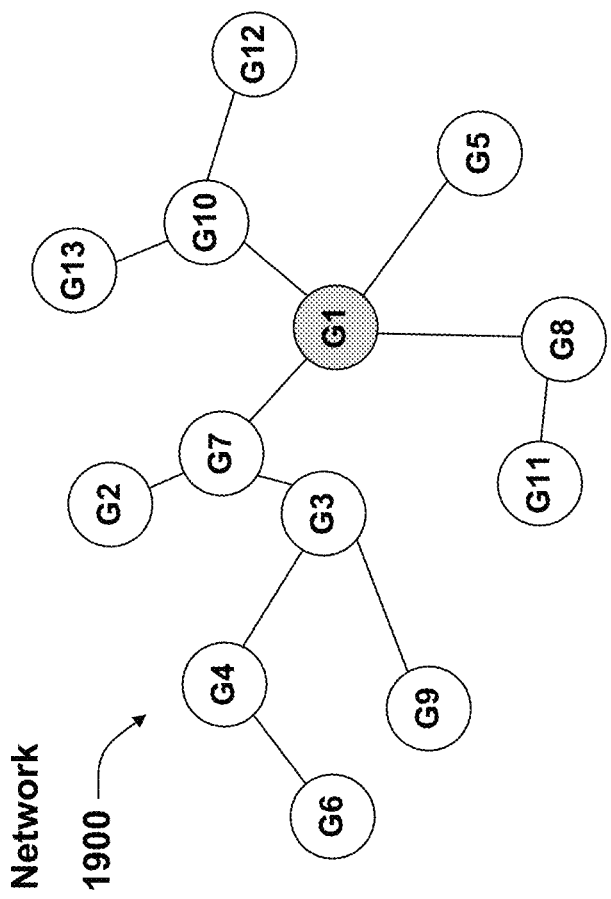
FIG. 19 shows a network of genes and the algorithms for obtaining interactome scores implementing a process.
Figure 20:
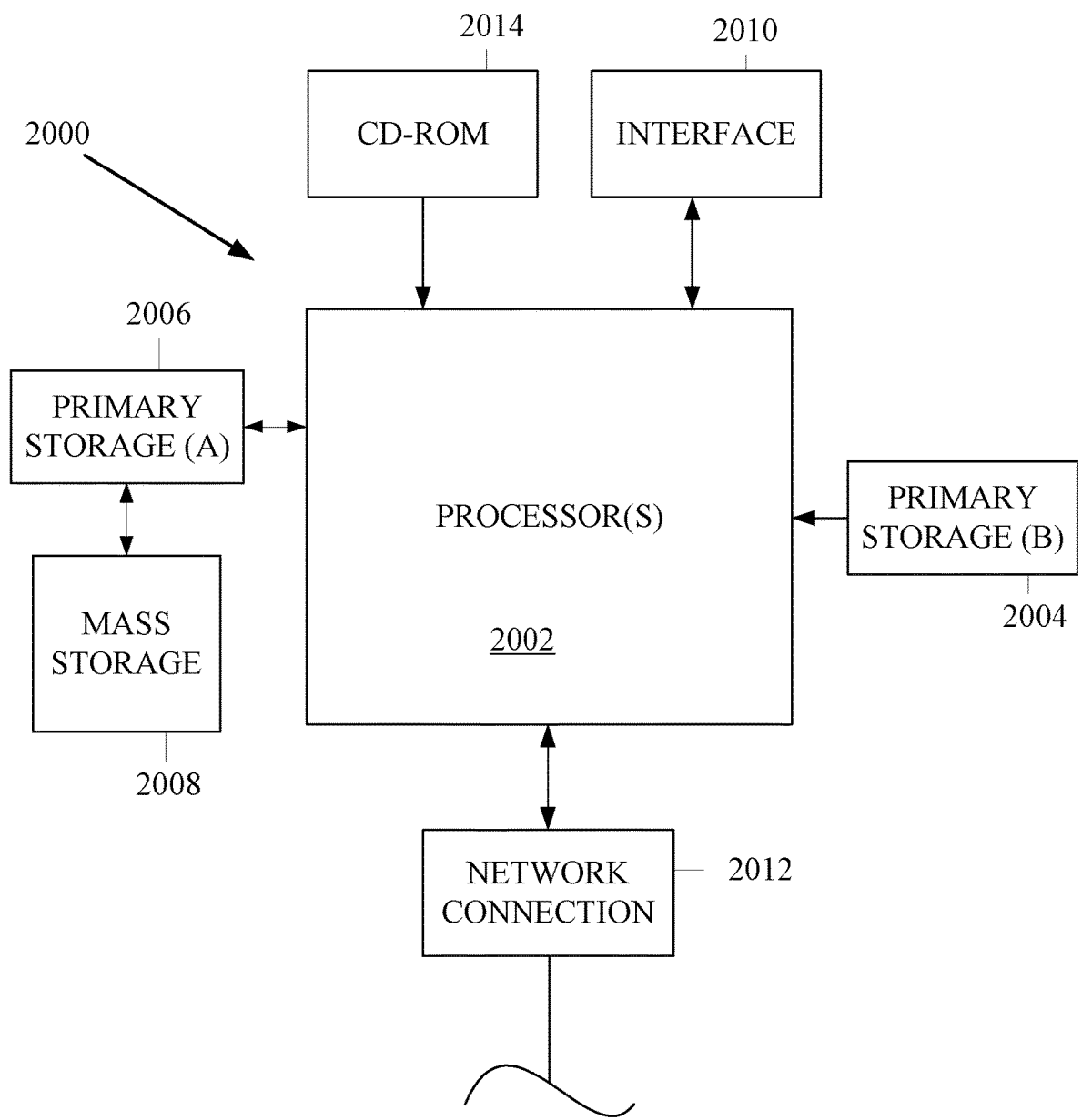
FIG. 20 is a diagrammatic representation of a computer system that can be used with the methods and apparatus described herein.

FIG. 19 shows a network of genes and the algorithms for obtaining interactome scores implementing process 1800.

Process 1800 further involves assigning a weight to each edge connecting two genes based on connection data for the two genes in at least one interactome knowledge base. In some implementations, the weight of the edge is proportional to the number of connections in the interactome knowledge base. In some implementations, the weight is proportional to other quantitative measures of the connection of the two genes according to the interactome knowledge base. See block 1804.

Process 1800 further involves calculating, for each gene in the network, and interactome score using (i) weights of edges between a particular gene and other genes connected to the particular gene, and (ii) summary scores of all genes connected to the particular gene. See block 1806. In some implementations, the interactome score is calculated as:

$$S'Gi \sim SGi + \Sigma((SGi+SGn)*EdgeWeight_n)$$

wherein $S'Gi$ is an interactome score for gene $Gi$, $SGi$ is a summary score for gene $Gi$, $SGn$ is a summary score for gene $Gn$ that is directly connected to $Gi$, and $EdgeWeight_n$ is a weight assigned to the edge connecting $Gi$ and $Gn$ based on knowledge based data.

Process 1800 further involves saving interactome scores that are smaller than a second threshold in a first pass dictionary. See block 1808. Process 1800 then proceeds to update the interactome scores by repeating the calculation of interactome scores for all genes in the first pass dictionary. See 1810. Process further 1800 involves determining whether to repeat for an additional pass of dictionary. See block 8012. If so, the process returns to block 1808, and saves interactome scores that are smaller a threshold in the second pass dictionary, and then update the interactome scores by repeating the calculation of interactome scores for all genes in the second pass dictionary. If the process determines not to further expand the interactome scores for the network, the process ends at 1814. The process of 1800 starts by computing interactome scores for genes that have high relatively high experimental values and strong connections. The process descends until even threshold is reached, thereby accessing notes with no experimental data assigned. The process then reevaluates the network strength by interaction to other nodes with higher experimental weight values.

Dampening Genes in Random Genes

It has been observed that certain genes appear to be randomly or unspecifically associated with various phenotypes. These genes may be considered random background genes in certain context. It is thus desirable to control the effects of these random background genes in order to more effectively identify relevant and important genes for phenotype or other concepts of interest. For instance, some cytokines tend to have high correlation with a cancer as a response to cancer cells, but their values for understanding the cause of cancers may be limited.

If the random gene sets are truly random, there should be little structure or correlation between the genes of the gene sets and the phenotype of interest. Conversely, if a gene has a significant correlation with the phenotype, regardless of the randomness of the gene set, its correlation with a concept of interest may not be meaningful for understanding the underlying mechanism.

In some implementations, random gene sets are sampled from the database. Rank lists of the genes from the random gene sets can be obtained. Some implementations then obtain the products of the ranks for the genes in the random gene sets. The rank product comprises a product of ranks of the particular gene across the one or more random gene sets. The ranks are based on the particular genes correlation with the biological, chemical, or medical concept of interest.

In some implementations, the methods also involve calculating a p value of the rank product, the p value indicating the probability of obtaining the rank product value by chance if the gene or set is not correlated with the phenotype. In some implementations, the method further involves applying a damping weight to the gene score of the gene based on the p value.

In some implementations the summary scores of the first and second one or more genes are penalized based on how likely experimental values of the first and second one or more genes in one or more random gene sets are correlated with the biological, chemical, or medical concept of interest. In some implementations, each summary score of a particular gene is penalized by a penalty value that is inversely proportional to the p value of the rank product. For instance, the dampening weight epsilon can be defined as epsilon $\sim p^{-1}$ or epsilon $\sim \log(abs(p^{-1}))$.

Computer System

As should be apparent, certain embodiments of the invention employ processes acting under control of instructions and/or data stored in or transferred through one or more computer systems. Certain embodiments also relate to an apparatus for performing these operations. This apparatus may be specially designed and/or constructed for the required purposes, or it may be a general-purpose computer selectively configured by one or more computer programs and/or data structures stored in or otherwise made available to the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines is shown and described below.

In addition, certain embodiments relate to computer readable media or computer program products that include program instructions and/or data (including data structures) for performing various computer-implemented operations associated with at least the following tasks: (1) obtaining raw data from instrumentation, databases (private or public (e.g., NCBI), and other sources, (2) curating raw data to provide Feature Sets, (3) importing Feature Sets and other data to a repository such as database or Knowledge Base, (4) mapping Features from imported data to pre-defined Feature references in an index, (5) generating a pre-defined feature index, (6) generating correlations or other scoring between Feature Sets and Feature Sets and between Feature Sets and Feature Groups, (7) creating Feature Groups, (8) generating concept scores or other measures of concepts relevant to features, Feature Sets and Feature Groups, (9) determining authority levels to be assigned to a concept for every feature, Feature Set and Feature Group that is relevant to the concept, (10) filtering by data source, organism, authority level or other category, (11) receiving queries from users (including, optionally, query input content and/or query field of search limitations), (12) running queries using features, Feature Groups, Feature Sets, Studies, concepts, taxonomy groups, and the like, and (13) presenting query results to a user (optionally in a manner allowing the user to navigate through related content perform related queries). The invention also pertains to computational apparatus executing instructions to perform any or all of these tasks. It also pertains to computational apparatus including computer readable media encoded with instructions for performing such tasks.

Further the invention pertains to useful data structures stored on computer readable media. Such data structures include, for example, Feature Sets, Feature Groups, taxonomy hierarchies, feature indexes, Score Tables, and any of the other logical data groupings presented herein. Certain embodiments also provide functionality (e.g., code and processes) for storing any of the results (e.g., query results) or data structures generated as described herein. Such results or data structures are typically stored, at least temporarily, on a computer readable medium such as those presented in the following discussion. The results or data structures may also be output in any of various manners such as displaying, printing, and the like.

Examples of displays suitable for interfacing with a user in accordance with the invention include but are not limited to cathode ray tube displays, liquid crystal displays, plasma displays, touch screen displays, video projection displays, light-emitting diode and organic light-emitting diode displays, surface-conduction electron-emitter displays and the like. Examples of printers include toner-based printers, liquid inkjet printers, solid ink printers, dye-sublimation printers as well as inkless printers such as thermal printers. Printing may be to a tangible medium such as paper or transparencies.

Examples of tangible computer-readable media suitable for use computer program products and computational apparatus of this invention include, but are not limited to, magnetic media such as hard disks, floppy disks, and magnetic tape; optical media such as CD-ROM disks; magneto-optical media; semiconductor memory devices (e.g., flash memory), and hardware devices that are specially configured to store and perform program instructions, such as read-only memory devices (ROM) and random access memory (RAM) and sometimes application-specific integrated circuits (ASICs), programmable logic devices (PLDs) and signal transmission media for delivering computer-readable instructions, such as local area networks, wide area networks, and the Internet. The data and program instructions provided herein may also be embodied on a carrier wave or other transport medium (including electronic or optically conductive pathways). The data and program instructions of this invention may also be embodied on a carrier wave or other transport medium (e.g., optical lines, electrical lines, and/or airwaves).

Examples of program instructions include low-level code, such as that produced by a compiler, as well as higher-level code that may be executed by the computer using an interpreter. Further, the program instructions may be machine code, source code and/or any other code that directly or indirectly controls operation of a computing machine. The code may specify input, output, calculations, conditionals, branches, iterative loops, etc.

FIG. 9 illustrates, in simple block format, a typical computer system that, when appropriately configured or designed, can serve as a computational apparatus according to certain embodiments. The computer system 2000 includes any number of processors 2002 (also referred to as central processing units, or CPUs) that are coupled to storage devices including primary storage 2006 (typically a random access memory, or RAM), primary storage 2004 (typically a read only memory, or ROM). CPU 2002 may be of various types including microcontrollers and microprocessors such as programmable devices (e.g., CPLDs and FPGAs) and non-programmable devices such as gate array ASICs or general-purpose microprocessors. In the depicted embodiment, primary storage 2004 acts to transfer data and instructions uni-directionally to the CPU and primary storage 2006 is used typically to transfer data and instructions in a bi-directional manner. Both of these primary storage devices may include any suitable computer-readable media such as those described above. A mass storage device 2008 is also coupled bi-directionally to primary storage 2006 and provides additional data storage capacity and may include any of the computer-readable media described above. Mass storage device 2008 may be used to store programs, data and the like and is typically a secondary storage medium such as a hard disk. Frequently, such programs, data and the like are temporarily copied to primary memory 2006 for execution on CPU 2002. It will be appreciated that the information retained within the mass storage device 2008, may, in appropriate cases, be incorporated in standard fashion as part of primary storage 2004. A specific mass storage device such as a CD-ROM 2014 may also pass data uni-directionally to the CPU or primary storage.

CPU 2002 is also coupled to an interface 2010 that connects to one or more input/output devices such as such as video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, C P U 2002 optionally may be coupled to an external device such as a database or a computer or telecommunications network using an external connection as shown generally at 2012. With such a connection, it is contemplated that the CPU might receive information from the network, or might output information to the network in the course of performing the method steps described herein.

In one embodiment, a system such as computer system 900 is used as a data import, data correlation, and querying system capable of performing some or all of the tasks described herein. System 900 may also serve as various other tools associated with Knowledge Bases and querying such as a data capture tool. Information and programs, including data files can be provided via a network connection 2012 for access or downloading by a researcher. Alternatively, such information, programs and files can be provided to the researcher on a storage device.

In a specific embodiment, the computer system 900 is directly coupled to a data acquisition system such as a microarray or high-throughput screening system that captures data from samples. Data from such systems are provided via interface 2010 for analysis by system 900. Alternatively, the data processed by system 900 are provided from a data storage source such as a database or other repository of relevant data. Once in apparatus 900, a memory device such as primary storage 2006 or mass storage 2008 buffers or stores, at least temporarily, relevant data. The memory may also store various routines and/or programs for importing, analyzing and presenting the data, including importing Feature Sets, correlating Feature Sets with one another and with Feature Groups, generating and running queries, etc.

In certain embodiments user terminals may include any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms. A server system in communication with a user terminal may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

EXAMPLES

Example 1

Example 1 investigates the effect of genes that are correlated with the phenotype in the random gene sets vs. gene sets that are specific to the phenotype. Also investigated are the effects of bootstrapping.

Figure 21A:
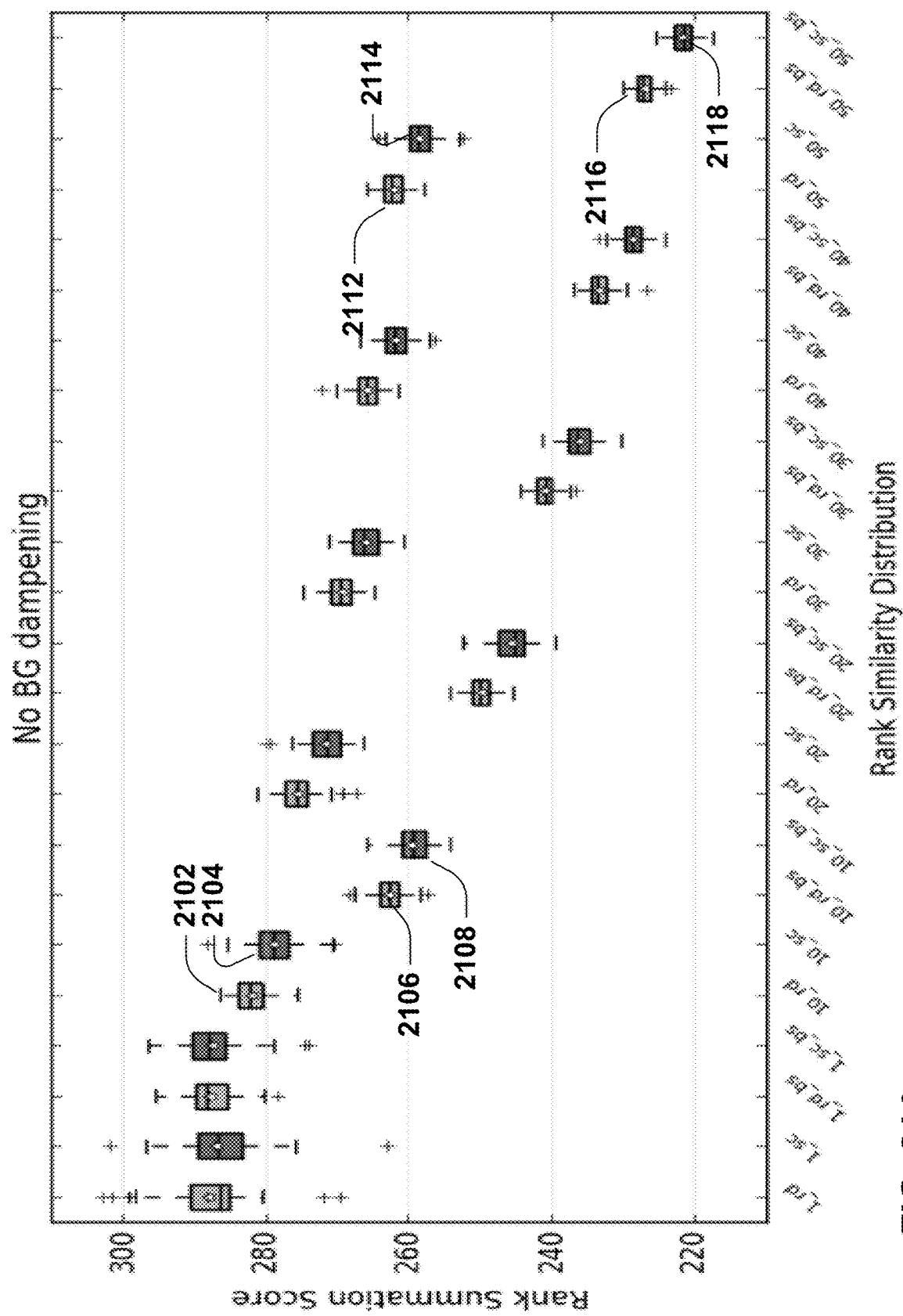
FIG. 21A and FIG. 21B show data illustrative summary score of genes that are correlated with the phenotype in the random gene sets vs. gene sets that are specific to the phenotype. It also shows the effects of bootstrapping.

For the group involving the random gene sets, random set of a plurality of random gene sets are randomly chosen from the database, and the summary scores are obtained for genes in the random gene sets. The results of random gene sets a shown in FIG. 21A at 2102, 2106, 2012, and 2016. The result at 2102 is obtained from 10 random gene sets without bootstrapping. The result at 2106 is obtained from 10 random gene sets with bootstrapping. The result at 2112 is obtained from 50 random gene sets without bootstrapping. The result at 2016 is obtained from 50 random gene sets with bootstrapping.

The results of phenotype specific gene sets are shown at 2104, 2108, 2114, and 2118. The result at 2104 is obtained from 10 phenotype specific gene sets without bootstrapping. The result at 2108 is obtained from data from 10 phenotype specific gene sets with bootstrapping. The result at 2114 is obtained from data of 50 phenotype specific gene sets without bootstrapping, and the result at 2118 is obtained from 50 phenotype specific gene sets with bootstrapping. As it is clear from FIG. 21A, the difference of the summary scores between the training set and the validation set increases as the size of the sample becomes larger. Moreover, bootstrapping provides significant improvements of the summary score difference as seen at the differential between 2112 and 2114 on the one hand, and 2116 and 2118 on the other hand. Furthermore, the phenotype specific gene sets have lower summary difference scores, indicating improvements of the model's reliability when the scores are based on genotype specific gene sets according to the processes described above.

Figure 21B:
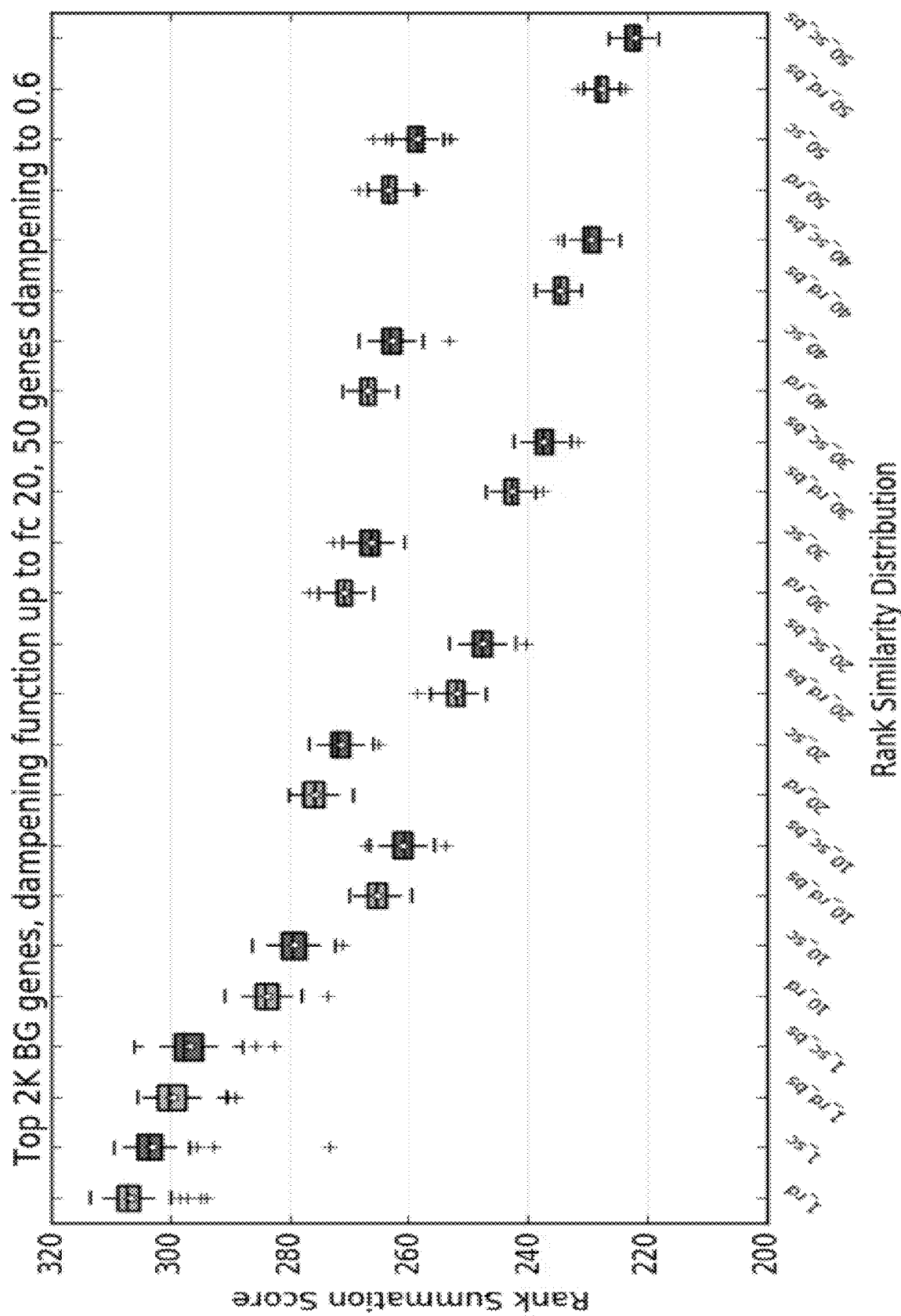

The data suggest that it would be probably beneficial to remove the effects from some genes in the random gene sets. FIG. 21B appears to support this hypothesis. FIG. 21B shows the data after the summary scores have been corrected according to some implementations described above. In the implementations, the summary scores of the genes are penalized or dampened based on the p scores of the rank products of the genes in the random gene sets, the penalty being inversely correlated with the piece scores. The data here show that the summary score difference decreases more rapidly than without dampening as the number of genes increases.

Example 2: Improvements Over Existing Technology

Methods and systems disclosed herein provide a processing framework that use experimental gene data, in silico gene data, and/or knowledge-based data to identify genes for concepts of interest. Components of the framework further includes serious novel features described above. This example compares the results from implementations of the disclosure to conventional methods that do not include multiomics or polyomics data or other novel features described above.

First, a same set of experimental data are provided to a conventional method and to a method according to some implementations to identify genes that are potentially associated with colon cancer. This comparison shows that although the results are not identical between the two methods, the top 46 genes that were identified by the conventional method shown in the table below largely coincide with the top 2% genes identified by the method according to some implementations.

| Genes Score | Genes | # Studies | Effect on Query | In Top 2% |
|---|---|---|---|---|
| −99.9095344 | CA1 | 15 | down-regulated | BG |
| −98.86549471 | GCG | 15 | down-regulated | TRUE |
| −97.42360942 | ZG16 | 16 | down-regulated | FALSE |
| −95.78159354 | CLCA4 | 13 | down-regulated | TRUE |
| −95.33909969 | CLDN8 | 9 | down-regulated | TRUE |
| −95.28165809 | SLC4A4 | 17 | down-regulated | BG |
| 93.92260836 | IL8 | 12 | up-regulated | BG |
| −93.07126892 | AQP8 | 13 | down-regulated | TRUE |
| −92.0476347 | MS4A12 | 13 | down-regulated | TRUE |
| 91.99080132 | INHBA | 12 | up-regulated | FALSE |
| −90.28012572 | GUCA2A | 15 | down-regulated | TRUE |
| 89.79450502 | REG1B | 10 | up-regulated | TRUE |
| −89.31131541 | UGT2B17 | 12 | down-regulated | TRUE |
| −88.92002216 | CA4 | 14 | down-regulated | BG |
| −88.8648738 | GUCA2B | 16 | down-regulated | TRUE |
| 88.41615842 | MMP3 | 15 | up-regulated | BG |
| 88.12870833 | KIAA1199 | 12 | up-regulated | BG |
| −87.52538637 | PYY | 13 | down-regulated | TRUE |
| 86.82538535 | FOXQ1 | 9 | up-regulated | BG |
| 85.07750478 | MMP1 | 14 | up-regulated | BG |
| −84.52351137 | CEACAM7 | 15 | down-regulated | TRUE |
| −83.97114504 | MT1M | 13 | down-regulated | BG |
| 83.68285944 | REG1A | 11 | up-regulated | TRUE |
| 83.67112035 | MMP7 | 13 | up-regulated | TRUE |
| −83.02756091 | ADH1C | 14 | down-regulated | TRUE |
| 82.15670582 | CXCL5 | 7 | up-regulated | BG |
| −82.10592173 | ITLN1 | 9 | down-regulated | TRUE |
| −82.07322339 | CALD1 | 9 | down-regulated | BG |
| −81.78194363 | HMGCS2 | 13 | down-regulated | TRUE |
| −81.71044711 | CD177 | 12 | down-regulated | BG |
| −80.66475862 | DHRS9 | 14 | down-regulated | BG |
| −80.1757188 | ABCA8 | 15 | down-regulated | TRUE |
| 79.33757769 | KRT23 | 10 | up-regulated | TRUE |
| −78.38441039 | SI | 8 | down-regulated | TRUE |
| −78.00592105 | ABCG2 | 14 | down-regulated | TRUE |
| 77.9242816 | CLDN1 | 10 | up-regulated | BG |
| −77.68595321 | TMEM47 | 5 | down-regulated | TRUE |
| 77.61251393 | CDH3 | 16 | up-regulated | TRUE |
| −77.48044528 | LGALS2 | 13 | down-regulated | BG |
| −77.44926173 | COL5A1 | 7 | down regulated | BG |
| 77.35276386 | CXCL1 | 13 | up-regulated | BG |
| −77.29479425 | PKIB | 11 | down-regulated | BG |
| 77.26880564 | TACSTD2 | 11 | up-regulated | BG |
| −77.20933478 | FCGBP | 12 | down-regulated | TRUE |
| −77.08712192 | AKR1B10 | 12 | down-regulated | FALSE |
| 77.00713203 | CTHRC1 | 9 | up-regulated | BG |

Second, experimental data are provided to the conventional method and the method according to some implementations to identify genes that are potentially associated with autism. This comparison shows that many genes in the top 100 genes identified by the method according to some implementations include many genes not identified by the conventional method. The table below includes the top 100 genes identified by the instant method.

| Genename | Score norm. | Score | 0.95 CI min | .95 CI max |
|---|---|---|---|---|
| LOC100132941 | 1 | 34.6 | −3.17 | −0.04 |
| IGHV3-30 | 0.94 | 33.02 | −3.02 | −0.04 |
| 5LC25A39 | 0.93 | 27.46 | −2.96 | −0.59 |
| SOS1 | 0.92 | 31.25 | −2.89 | −0.07 |
| LOC390714 | 0.85 | 29.45 | −2.7 | −0.03 |
| EN5G00000224650 | 0.85 | 29.67 | −2.72 | −0.04 |
| RTN4 | 0.81 | 28.22 | −2.32 | 0.28 |
| LOC401847 | 0.81 | 27.64 | −2.43 | 0.1 |
| RP524 | 0.8 | 23.48 | −0.34 | 1.84 |
| NLGN4Y | 0.79 | 30.34 | −0.25 | 2.54 |
| CREB1 | 0.78 | 20.61 | −0.43 | 1.5 |
| OPHN1 | 0.77 | 24.17 | −2.22 | −0.03 |
| SCN1B | 0.77 | 30.55 | −2.83 | −0.07 |
| FCRL5 | 0.76 | 22.35 | −1.93 | 0.12 |

-continued

| Genename | Score norm. | Score | 0.95 CI min | .95 CI max |
|---|---|---|---|---|
| RNASE3 | 0.74 | 25.73 | −1.2 | 1.24 |
| IGHA2 | 0.72 | 27.22 | −2.39 | 0.09 |
| RAB2B | 0.72 | 24.04 | −2.23 | −0.06 |
| GRAPL | 0.72 | 23.46 | −2.2 | −0.09 |
| FAM181B | 0.71 | 23.19 | 0.26 | 2.31 |
| CAMK2D | 0.7 | 19.6 | −1.62 | 0.19 |
| KLF1 | 0.7 | 24.84 | −2.14 | 0.13 |
| ACTN1 | 0.7 | 19.98 | −2.05 | −0.3 |
| HAPLN4 | 0.69 | 29.9 | −2.53 | 0.21 |
| TP53BP2 | 0.69 | 24.71 | −0.39 | 1.91 |
| SH2D1B | 0.68 | 21.81 | 0.25 | 2.18 |
| GAD2 | 0.68 | 24.24 | −2.07 | 0.16 |
| SLC7A3 | 0.68 | 24.1 | −0.08 | 2.12 |
| TRIM58 | 0.68 | 23.64 | −2.08 | 0.08 |
| ENSG00000244575 | 0.67 | 27.21 | −2.31 | 0.18 |
| FGFR1OP2 | 0.67 | 23.06 | −1.68 | 0.47 |
| SNORD3A | 0.67 | 25.89 | −0.37 | 2.04 |
| COX7B | 0.66 | 20.69 | −0.36 | 1.57 |
| KCNK2 | 0.66 | 21.37 | −1.58 | 0.42 |
| C10orf85 | 0.66 | 25.22 | −0.46 | 1.89 |
| ENSG00000226054 | 0.65 | 18.06 | −2.4 | −1.06 |
| PSMF1 | 0.65 | 20.9 | −1.93 | −0.05 |
| GSTM1 | 0.65 | 17.41 | −0.54 | 1.11 |
| ZNF148 | 0.64 | 18.91 | −1.51 | 0.24 |
| ENSG00000226058 | 0.64 | 17.86 | −2.37 | −1.05 |
| PCMTD1 | 0.64 | 19.19 | −1.5 | 0.29 |
| ENSG00000226049 | 0.64 | 17.63 | −2.33 | −1.02 |
| CPLX1 | 0.64 | 26.35 | −2.41 | −0.03 |
| FOXP1 | 0.64 | 18.7 | −1.61 | 0.1 |
| ENSG00000226057 | 0.64 | 17.74 | −2.36 | −1.05 |
| ENSG00000226056 | 0.63 | 17.71 | −2.34 | −1.02 |
| LOC389634 | 0.63 | 21.43 | −2.05 | −0.14 |
| ENSG00000226055 | 0.63 | 17.64 | −2.35 | −1.05 |
| C12orf68 | 0.63 | 23.34 | −2.14 | −0.03 |
| ENSG00000226050 | 0.63 | 17.41 | −2.32 | −1.03 |
| VSIG6 | 0.63 | 22.11 | −2.06 | −0.07 |
| ENSG00000226040 | 0.63 | 17.3 | −2.28 | −0.99 |
| EPB42 | 0.62 | 19.85 | −1.87 | −0.08 |
| ENSG00000226043 | 0.62 | 17.17 | −2.26 | −0.97 |
| ENSG00000226047 | 0.62 | 17.12 | −2.27 | −1 |
| ENSG00000226042 | 0.62 | 17.16 | −2.28 | −1.01 |
| ENSG00000226061 | 0.62 | 17.4 | −2.3 | −1 |
| ENSG00000226048 | 0.62 | 17.09 | −2.26 | −1 |
| ENSG00000226046 | 0.62 | 17.05 | −2.28 | −1.03 |
| C17orf97 | 0.62 | 20.14 | −1.48 | 0.4 |
| ENSG00000226045 | 0.62 | 17.07 | −2.25 | −0.98 |
| ENSG00000226041 | 0.62 | 17.06 | −2.26 | −1 |
| CLINT1 | 0.62 | 22.26 | −1.96 | 0.07 |
| JAKMIP1 | 0.62 | 24.61 | −0.2 | 2.06 |
| ENSG00000226044 | 0.61 | 16.93 | −2.24 | −0.98 |
| GPR146 | 0.61 | 18.78 | −1.87 | −0.21 |
| ENSG00000226059 | 0.61 | 17.16 | −2.29 | −1.03 |
| ALDH1L2 | 0.61 | 18.29 | −1.11 | 0.62 |
| ENSG00000226010 | 0.61 | 16.83 | −2.24 | −1 |
| ENSG00000226142 | 0.61 | 16.66 | −2.28 | −1.09 |
| ENSG00000226066 | 0.61 | 16.9 | −2.24 | −0.99 |
| ENSG00000226141 | 0.61 | 16.66 | −2.26 | −1.06 |
| ENSG00000226011 | 0.61 | 16.68 | −2.2 | −0.96 |
| ENSG00000226063 | 0.61 | 16.89 | −2.26 | −1.02 |
| ENSG00000226014 | 0.6 | 16.68 | −2.17 | −0.9 |
| ENSG00000226139 | 0.6 | 16.6 | −2.27 | −1.09 |
| ENSG00000226038 | 0.6 | 16.67 | −2.17 | −0.91 |
| ENSG00000226064 | 0.6 | 16.84 | −2.24 | −0.99 |
| ENSG00000226035 | 0.6 | 16.62 | −2.18 | −0.93 |
| ENSG00000226074 | 0.6 | 16.77 | −2.23 | −0.99 |
| ENSG00000226037 | 0.6 | 16.6 | −2.18 | −0.94 |
| ENSG00000226032 | 0.6 | 16.61 | −2.18 | −0.93 |
| SNORD28 | 0.6 | 21.57 | 0.01 | 1.97 |
| ENSG00000226012 | 0.6 | 16.59 | −2.19 | −0.96 |
| CARD16 | 0.6 | 18.29 | −0.57 | 1.16 |
| ENSG00000226013 | 0.6 | 16.56 | −2.17 | −0.93 |
| ENSG00000226078 | 0.6 | 16.68 | −2.21 | −0.98 |
| ENSG00000226034 | 0.6 | 16.54 | −2.15 | −0.89 |
| PTGDR | 0.6 | 20.61 | −0.76 | 1.19 |
| ENSG00000226036 | 0.6 | 16.5 | −2.16 | −0.92 |
| ENSG00000226022 | 0.6 | 16.55 | −2.19 | −0.96 |
| ENSG00000226028 | 0.6 | 16.51 | −2.16 | −0.93 |
| AMICA1 | 0.6 | 19.15 | −1.63 | 0.13 |
| ENSG00000226070 | 0.6 | 16.57 | −2.2 | −0.98 |
| ENSG00000226027 | 0.6 | 16.47 | −2.16 | −0.93 |
| ENSG00000226030 | 0.6 | 16.44 | −2.16 | −0.92 |
| TREML4 | 0.6 | 21.67 | −1.88 | 0.1 |
| ENSG00000226029 | 0.6 | 16.44 | −2.16 | −0.92 |
| ENSG00000226065 | 0.6 | 16.55 | −2.2 | −0.98 |
| ENSG00000226024 | 0.6 | 16.47 | −2.18 | −0.96 |
| ENSG00000226140 | 0.6 | 16.39 | −2.23 | −1.05 |

Among the above identified genes, many are not identified by the conventional method. More importantly, literature research confirmed that there are empirical evidence supporting association between these genes and autism. For examples, see Shi et al., Molecular Autism 2013, 4:8, confirming NOTCH2 link to autism; Bacon et al., Molecular Psychiatry (2015), 632-639, confirming FOXP1; and Nava et al., Amino Acids (2015) 47:2647-2658, confirming SLC7A3.

Although the foregoing invention has been described in some detail for purposes of clarity of understanding, it will be apparent that certain changes and modifications may be practiced within the scope of the invention. It should be noted that there are many alternative ways of implementing the processes and databases of the present invention. Accordingly, the present embodiments are to be considered as illustrative and not restrictive, and the invention is not to be limited to the details given herein.

What is claimed is:

1. A computer system, comprising:
   one or more processors;
   system memory;
   one or more computer-readable storage media having stored thereon a database comprising a plurality of gene sets, wherein each gene set of the plurality of gene sets comprises a plurality of genes and a plurality of experimental values associated with the plurality of genes, and wherein the plurality of experimental values are correlated with a biological, chemical, or medical concept of interest in at least one experiment; and
   one or more computer-readable storage media storing program code that, when executed by the one or more processors, causes the computer system to implement a method for identifying genes associated with the biological, chemical, or medical concept of interest, said program code comprising:
   (a) code for selecting the plurality of gene sets from the database;
   (b) code for determining, for each gene set, one or more experimental gene scores for first one or more genes among the plurality of genes using one or more experimental values of the first one or more genes;
   (c) code for determining, for each gene set, one or more in silico gene scores for second one or more genes among the plurality of genes based at least in part on the first one or more genes' correlations with the second one or more genes, wherein:
   the first one or more genes' correlations with the second one or more genes are indicated in other gene sets in the database beside the plurality of gene sets,
   each of the other gene sets comprises correlation scores between one or more of the second one or more genes and one of the first one or more genes, an in silico gene score for each of the second one or more genes indicates a correlation between each of the second one or more genes and one or more of the first one or more genes, and the in silico gene score for each of the second one or more genes is obtained by aggregating the correlation scores for each of the second one or more genes across the other gene sets;

(d) code for obtaining summary scores for the first and second one or more genes based at least in part on the one or more experimental gene scores for the first one or more genes determined in (b) and the one or more in silico gene scores for the second one or more genes determined in (c), wherein each summary score is aggregated across the plurality of gene sets; and (e) code for identifying the genes associated with the biological, chemical, or medical concept of interest using the summary scores of the first and second one or more genes.

2. The computer system of claim 1, wherein (c) comprises, for each gene set of the plurality of gene sets, (i) code for identifying a second plurality of gene sets from the database, each gene set of the second plurality of gene sets comprising a second plurality of genes and a second plurality of experimental values associated with the second plurality of genes, and wherein the second plurality of experimental values are correlated with a first gene among the first one or more genes;

(ii) code for aggregating the experimental values across the second plurality of gene sets to obtain a vector of aggregated values for the first gene among the first one or more genes;

(iii) code for applying (i) and (ii) to one or more other genes among the first one or more genes, thereby obtaining one or more vectors of aggregated values for the one or more other genes among the first one or more genes; and (iv) code for aggregating vectors of aggregated values for the first gene and the one or more other genes among the first one or more genes, thereby obtaining one compressed vector comprising the one or more in silico gene scores for the second one or more genes.

3. The computer system of claim 1, wherein said program code further comprising code for determining one or more gene-group scores for third one or more genes.

4. The computer system of claim 1, wherein said program code further comprising code for determining interactome scores respectively for fourth one or more genes.

5. A method, implemented at a computer system that includes one or more processors and system memory, for identifying genes associated with a biological, chemical, or medical concept of interest, the method comprising:

(a) selecting, by the one or more processors, a plurality of gene sets from a database, wherein each gene set of the plurality of gene sets comprises a plurality of genes and a plurality of experimental values associated with the plurality of genes, and wherein the plurality of experimental values are correlated with the biological, chemical, or medical concept of interest in at least one experiment;

(b) determining, for each gene set and by the one or more processors, one or more experimental gene scores for first one or more genes among the plurality of genes using one or more experimental values of the first one or more genes;

(c) determining, for each gene set and by the one or more processors, one or more in silico gene scores for second one or more genes among the plurality of genes based at least in part on the first one or more genes' correlations with the second one or more genes, wherein:

the first one or more genes' correlations with the second one or more genes are indicated in other gene sets in the database beside the plurality of gene sets, each of the other gene sets comprises correlation scores between one or more of the second one or more genes and one of the first one or more genes, an in silico gene score for each of the second one or more genes indicates a correlation between each of the second one or more genes and one or more of the first one or more genes, and the in silico gene score for each of the second one or more genes is obtained by aggregating the correlation scores for each of the second one or more genes across the other gene sets;

(d) obtaining, by the one or more processors, summary scores for the first and second one or more genes based at least in part on the one or more experimental gene scores for the first one or more genes determined in (b) and the one or more in silico gene scores for the second one or more genes determined in (c), wherein each summary score is aggregated across the plurality of gene sets; and (e) identifying, by the one or more processors, the genes associated with the biological, chemical, or medical concept of interest using the summary scores of the first and second one or more genes.

6. The method of claim 5, wherein (c) comprises, for each gene set of the plurality of gene sets, (i) identifying a second plurality of gene sets from the database, each gene set of the second plurality of gene sets comprising a second plurality of genes and a second plurality of experimental values associated with the second plurality of genes, and wherein the second plurality of experimental values are correlated with a first gene among the first one or more genes;

(ii) aggregating the experimental values across the second plurality of gene sets to obtain a vector of aggregated values for the first gene among the first one or more genes;

(iii) applying (i) and (ii) to one or more other genes among the first one or more genes, thereby obtaining one or more vectors of aggregated values for the one or more other genes among the first one or more genes; and (iv) aggregating vectors of aggregated values for the first gene and the one or more other genes among the first one or more genes, thereby obtaining one compressed vector comprising the one or more in silico gene scores for the second one or more genes.

7. The method of claim 5, further comprising, determining, before (d), one or more gene-group scores for third one or more genes.

8. The method of claim 7, wherein each gene-group score for a particular gene is determined using (i) gene memberships of one or more gene groups that each comprise a group of genes related to a group label, wherein the group of genes comprises the particular gene, and (ii) at least some of the one or more experimental values of the first one or more genes.

9. The method of claim 8, wherein (d) comprises obtaining the summary scores for the first and second one or more genes based at least in part on the gene-group scores for at least some of the third one or more genes, as well as the one or more experimental scores for the first one or more genes determined in (b) and the one or more in silico scores for the second one or more genes determined in (c).

10. The method of claim 8, wherein determining the one or more gene-group scores for the third one or more genes comprises:
identifying, for a particular gene among the third one or more genes, the one or more gene groups that each comprise the particular gene;
determining, for each gene group, a percentage of members of the gene group that are among the first one or more genes;
aggregating, for each gene group, one or more experimental values of at least some of the first one or more genes that are members of the gene group, thereby obtaining a sum experimental value for the gene group; and
determining, for the particular gene among the third one or more genes, a gene-group score using the percentage of members of the gene group that are among the first one or more genes and the sum experimental value for the gene group.

11. The method of claim 10, wherein determining the gene-group score using the percentage of members of the gene group that are among the first one or more genes and the sum experimental value for the gene group comprises:
obtaining, for each gene group, a product of the percentage of members and the sum experimental value, thereby obtaining one or more products for the one or more gene groups;
summing, across the one or more gene groups, the one or more products, thereby obtaining a summed product; and
determining, for the particular gene among the third one or more genes, a gene-group score based on the summed product.

12. The method of claim 5, further comprising, before (d), determining interactome scores respectively for fourth one or more genes.

13. The method of claim 12, wherein each interactome score for a particular gene is determined using (i) connections between the particular gene and other genes connected to the particular gene in a network of genes and (ii) at least some of the one or more experimental values of the first one or more genes.

14. The method of claim 13, wherein (d) comprises obtaining the summary scores for at least the first one or more genes and the second one or more genes based at least in part on the interactome scores for at least some of the fourth one or more genes, as well as the one or more experimental gene scores for the first one or more genes determined in (b) and the one or more in silico gene scores for the second one or more genes determined in (c).

15. The method of claim 13, wherein the network of genes are based on interactions and relations among genes, proteins, and/or phospholipids.

16. The method of claim 13, wherein determining interactome scores respectively for the fourth one or more genes comprises:
providing a network of genes, wherein each pair of genes in the network are connected by an edge, the genes of the network comprise the fourth one or more genes, which comprise at least some of the first one or more genes and/or the second one or more genes;
defining, for each gene of the fourth one or more genes, a neighborhood of connected genes based on a connection distance from a particular gene as measured by the number of connection edges connecting two adjacent genes; and
calculating, for each gene of the fourth one or more genes, an interactome score using (i) one or more connection distances between the particular gene and one or more other genes in the neighborhood of connected genes and (ii) summary scores of the one or more other genes in the neighborhood of connected genes, wherein the summary scores are based on experimental data.

17. The method of claim 16, wherein the interactome score is calculated as proportional to a sum of multiple fractions, each fraction being a summary score of another gene in the neighborhood of connected genes divided by a connection distance between the particular gene and the other gene in the neighborhood of connected genes.

18. The method of claim 13, wherein determining interactome scores respectively for the fourth one or more genes comprises:
providing a network of genes, wherein the genes of the network have summary scores based on experimental data above a first threshold value, each pair of genes are connected by an edge, and the genes of the network comprise the fourth one or more genes, which comprise at least some of the first one or more genes and/or the second one or more genes;
assigning, for each edge, a weight to the edge connecting two genes based on connection data for the two genes in at least one intereactome knowledge base; and
calculating, for each gene in the network, an interactome score using (i) weights of edges between a particular gene and all genes connected to the particular gene, and (ii) summary scores of all genes connected to the particular gene.

19. The method of claim 18, wherein calculating the interactome score comprises calculating the interactome score as $N_i'$:

$$N_i' = N_i + \Sigma((N_i + N_n) * \text{edge\_weight}_n)$$

wherein $N_i$ is the summary score of the particular gene i, $N_n$ is a summary score of gene n connected to the particular gene, and $\text{edge\_weight}_n$ is the weight of the edge connecting the particular gene i and gene n.

20. The method of claim 19, wherein calculating the interactome score further comprises:
saving $N_i'$ that are smaller than a second threshold in a first pass dictionary; and
repeating the calculating of claim 19 for all genes in the first pass dictionary, thereby updating the interactome scores.

21. The method of claim 20, wherein calculating the interactome score further comprises repeating the operations of claim 20 for one or more passes.

22. The method of claim 5, wherein selecting the plurality of gene sets of (a) comprises selecting gene sets based on biotag scores assigned to biotags associated with the gene sets, wherein the biotag scores indicate levels of importance of the gene sets.

23. The method of claim 22, wherein the biotags are organized by categories selected from a group consisting of biosource, biodesign, tissue, disease, compound, gene, genemode, biogroup, and any combination thereof.

24. The method of claim 5, wherein the plurality of experimental values comprises a plurality of gene perturbation values.

25. The method of claim 6, wherein the plurality of experimental values indicates levels of RNA expression, protein expression, DNA methylation, transcription factor activity, and/or association in genome wide association study.

26. The method of claim 5, wherein the biological, chemical, or medical concept of interest comprises a phenotype.

27. The method of claim 26, wherein the phenotype comprises a disease-related phenotype.

28. The method of claim 5, wherein the summary scores of the first and second one or more genes are penalized based on how likely experimental values of the first and second one or more genes in one or more random gene sets are correlated with the biological, chemical, or medical concept of interest.

29. A computer program product comprising a non-transitory machine readable medium storing program code that, when executed by one or more processors of a computer system, causes the computer system to implement a method for identifying genes associated with a biological, chemical, or medical concept of interest, said program code comprising:
  (a) code for selecting a plurality of gene sets from a database, wherein each gene set of the plurality of gene sets comprises a plurality of genes and a plurality of experimental values associated with the plurality of genes, and wherein the plurality of experimental values are correlated with the biological, chemical, or medical concept of interest in at least one experiment;
  (b) code for determining, for each gene set, one or more experimental gene scores for first one or more genes among the plurality of genes using one or more experimental values of the first one or more genes;
  (c) code for determining, for each gene set, one or more in silico gene scores for second one or more genes among the plurality of genes based at least in part on the first one or more genes' correlations with the second one or more genes, wherein:
    the first one or more genes' correlations with the second one or more genes are indicated in other gene sets in the database beside the plurality of gene sets,
    each of the other gene sets comprises correlation scores between one or more of the second one or more genes and one of the first one or more genes,
    a in silico gene score for each of the second one or more genes indicates a correlation between each of the second one or more genes and one or more of the first one or more genes, and
    the in silico gene score for each of the second one or more genes is obtained by aggregating the correlation scores for each of the second one or more genes across the other gene sets;
  (d) code for obtaining summary scores for the first and second one or more genes based at least in part on the one or more experimental gene scores for the first one or more genes determined in (b) and the one or more in silico gene scores for the second one or more genes determined in (c), wherein each summary score is aggregated across the plurality of gene sets; and
  (e) code for identifying the genes associated with the biological, chemical, or medical concept of interest using the summary scores of the first and second one or more genes.

* * * * *